United States Patent [19]
Donelick

[11] Patent Number: 5,267,274
[45] Date of Patent: Nov. 30, 1993

[54] METHOD OF FISSION TRACK ANALYSIS UTILIZING BULK CHEMICAL ETCHING OF APATITE

[76] Inventor: Raymond A. Donelick, 4819 Katy Hockley Rd., Katy, Tex. 77493

[21] Appl. No.: 891,847

[22] Filed: May 29, 1992

[51] Int. Cl.$^5$ ............................................... G21G 1/06
[52] U.S. Cl. ................................... 376/164; 376/158; 250/253; 250/260; 356/30
[58] Field of Search ...................... 376/158, 160, 164; 250/253, 260, 391; 356/30

[56] References Cited

U.S. PATENT DOCUMENTS

| | | | |
|---|---|---|---|
| 1,799,604 | 4/1931 | Read | 356/30 |
| 4,093,420 | 6/1978 | Grayson | 23/230 |
| 4,167,109 | 9/1979 | Gold | 73/15 R |
| 4,906,093 | 3/1990 | Trossarelli | 356/30 |
| 4,925,298 | 5/1990 | Dobrilla | 356/30 |

*Primary Examiner*—Donald P. Walsh
*Assistant Examiner*—Frederick H. Voss
*Attorney, Agent, or Firm*—Keeling & Associates

[57] ABSTRACT

A method of analysis of rock samples taken from the bore of a well being drilled or from the Earth's surface and performed upon the apatite grains contained within the samples. The apatite grains are separated from the surrounding rock, polished to expose internal surfaces, and etched with acid to reveal the presence and characteristics of fission tracks within the apatite to determine the geological characteristics of the apatite. The grains containing the apatite are viewed under an optical microscope or other imaging apparatus and apatite crystals or crystal fragments which contain etched fission tracks are selected for analysis. If selected for analysis, measurements may be taken to determine the size and shape of the etched pits intersecting the apatite grain surface. The measurements are taken using a digitizing apparatus interconnected to a computer and containing a point light source superimposed upon the apatite grains viewed through the microscope. The measurements are used to determine the chemical composition of the apatite and in conjunction with data gathered by already existing methods, the fission track age and distribution of perceived track lengths for the fluorine-rich apatite grains are calculated. Determining chemical composition of apatite by this method eliminates procedures which are labor intensive, lengthy, costly, and potentially hazardous. The data derived from the analysis of the etched fission tracks are used as input criteria for existing kinetic modelling programs currently in use to constrain the temperature history of the apatite grains.

32 Claims, 15 Drawing Sheets

METHOD OF FISSION TRACK ANALYSIS UTILIZING BULK CHEMICAL ETCHING OF APATITE

BACKGROUND OF THE INVENTION

1. Field of the Invention

This invention relates to a method of determining the chemical composition of apatite grains contained within rock samples taken from the bore of a well being drilled or from the surface of the Earth.

2. Description of the Prior Art

Numerous methods of analyzing the chemical composition of minerals have been used including the currently used method of using a microprobe to focus a beam of electrons onto the surface of a material and causing X-rays to be generated. By carefully monitoring the X-rays emitted during the bombardment of a surface by the electron beam, it is possible to determine the chemical composition of the material being bombarded.

Presently, in the oil exploration field, it is desirous to identify apatite grains contained within rocks which are rich in fluorine in order to perform analyses on them for purposes of determining the thermal history of the rock. This is most often accomplished by grinding or crushing the rock sample to obtain sand-sized grains and then separating the grains containing apatite crystals from the surrounding grains of minerals and rock in a multiple stage process using the density and magnetic characteristics of the surrounding minerals.

After a multiple step process, the remaining grains of the rock sample consist of a sufficiently high percentage of apatite for purposes of analysis. A representative portion of the remaining apatite grains is then incorporated into an epoxy wafer attached to a petrographic slide, polished to expose internal surfaces, and etched with acid. The epoxy wafer is covered with a muscovite mica detector in the form of a mask and placed adjacent to the core of a nuclear reactor along with a uranium-doped glass covered with a second muscovite mica detector where both are irradiated with thermal neutrons. The epoxy wafer, uranium-doped glass, and their attached muscovite mica detectors are then removed from the reactor and the muscovite mica detectors are immersed in hydrofluoric acid to etch the induced fission tracks caused by the induced fission of uranium in the apatite grains and the uranium-doped glass. The concentration of $^{238}U$ and the fission track density per unit volume are determined for a volume of an apatite grain beneath a selected area of the apatite grain and the fission track age for each grain is determined.

In the methods currently practiced within the industry, the chemical composition of the apatite grains is then determined by a process known as microprobe analysis. This process consists of placing the apatite grains under an electron beam thereby inducing each affected apatite grain to produce X-rays. Through the careful monitoring and detection of these emitted X-rays, it is possible to determine whether the apatite grain being subjected to the electron beam is fluorine-rich, chlorine-rich, or water-rich, or some combination of these types.

The currently practiced process of determining the chemical composition of the apatite grains is an extremely costly, time consuming, and labor intensive process, and, as such, it is rarely done with sufficient completeness. Additionally, the level of expertise required of the person performing the actual steps of the analyses currently used is greater than in that of the present invention. The method of the present invention demands a high level of expertise only during the interpretation phase rather than during the actual performance of the analyses, consumes less time for a given number of samples, and results in greatly increased capital savings.

Read, U.S. Pat. No. 1,799,604 discloses a method and apparatus for identifying precious gems and crystals which operates upon the principle of an initial ray or beam of light striking a diamond and being reflected or refracted into secondary rays of light whose intensity and direction are dependent upon the angles, faces and imperfections in the diamond. This apparatus allows the recording of the secondary rays so that the diamond or crystal can be identified thereby under identical conditions.

Grayson, U.S. Pat. No. 4,093,420 discloses a method of prospecting for accumulations of minerals based upon organic material present in the rock samples taken at differing locations and depths. This method is based upon the amount of light emitted or absorbed by the specific organic particles within the rocks and the gradients between samples taken at the same location but at different depths are plotted on a map. By repeating this procedure for numerous locations, the contours which will appear on the map will encircle the mineral deposit.

Trossarelli, U.S. Pat. No. 4,906,093 discloses an illuminator device for the spectroscopic observation of samples wherein the substance under examination is illuminated by a source of white light and possesses optical fibers for transmitting the residual illumination light passed through the substance observed to an observation spectroscope.

Dobrilla, U.S. Pat. No. 4,925,298 discloses a method for measuring and plotting the etch pit density on the surface of an etched test wafer. In this method, a beam of light is focused onto an etched wafer and the intensity of the light reflected is compared with the intensity of a reference wafer to calculate the etch pit density of the etched wafer. This procedure is repeated for different areas of the etched wafer so that any variances within each wafer may be detected.

In the method of the present invention, the chemical composition of the apatite grains is determined by taking measurements of etch figures formed by the intersection of etched naturally occurring fission tracks or other crystallographic imperfections, such as other charged-particle tracks, defects, dislocations, fluid inclusions, mineral inclusions, polishing scratches, and fractures, with the planar surface of the apatite grain being observed. The purpose of the measurements is to determine if the apatite is of a fluorine-rich, chlorine-rich, or water-rich nature. Apatite grains which are fluorine-rich are identified by the characteristic dimensions of the etch figures within their etched planar surfaces.

The dimensions of the etch figures in fluorine-rich apatite and relatively non-fluorine-rich apatite are taken and, together with other information gathered by methods of analysis already used within the geological sector of the scientific community, the pooled fission track ages and the pooled distributions of perceived track lengths pertaining to the fluorine-rich apatite grains and the relatively non-fluorine-rich apatite grains, respectively, are determined.

While the prior art discloses methods and apparatus with which to observe mineral or rock samples and even calculate the density of etch pits on the surface of a wafer containing crystals which has been etched, the actual use of the dimensions of the resulting etch pits and the etch figures they form has not been practiced to determine chemical composition of the crystalline structure which has been etched.

SUMMARY OF THE INVENTION

It is an objective of this invention to provide a method for utilizing measurements of two-dimensional etch figures formed by the intersection of etched, naturally occurring fission tracks and other crystallographic imperfections with the surface of the apatite grain in which they exist to determine the chemical characteristics and composition of the apatite. Apatite grains are obtained from rock samples from the bore of a well or from the surface of the Earth for the purpose of determining the geological evolution of the rock samples. By observing and measuring the etch pits and the etch figures they form after exposing naturally occurring fission tracks and other crystallographic imperfections to acid, it may be determined whether the apatite grains being analyzed are predominantly fluorine-rich (or fluorapatite), chlorine-rich (or chlorapatite), or water-rich (or hydroxyapatite), and, using already existing methods, it will allow the pooled fission track ages and the pooled distributions of perceived track lengths to be determined for the predominantly fluorine-rich apatite grains and for the predominantly non-fluorine-rich apatite grains.

The present method utilizes the shape and dimensions of two-dimensional etch figures on etched planar surfaces of apatite grains in order to determine the chemical composition of apatite grains obtained from rock samples. Over time, fission tracks accumulate in the apatite grains due to the self-destruction of the nuclei of the trace element $^{238}U$. The fission that occurs when one of these nuclei spontaneously destructs causes damage to the surrounding crystalline structure of the host apatite grain. The resulting damage is an elongated path known as a fission track. While these fission tracks cannot be seen optically, they may be enlarged or etched, sufficiently to be viewed using either an optical microscope or a scanning-electron microscope, by exposing the planar surface of the apatite grain to an acidic solution and preferentially dissolving the crystallographic damage that constitutes the naturally occurring fission tracks. The etching process transforms fission tracks that intersect the etched planar surface of an apatite grain into etch pits. An etch pit is a polyhedral (or three-dimensional) recess issuing from the etched planar surface of the apatite grain; prior to becoming an etch pit, the space within the polyhedral recess was initially composed of apatite material that ultimately was preferentially dissolved by the acidic solution. An etch figure is the polygonal (or two-dimensional) cross-section of the etch pit where it intersects the etched planar surface of an apatite grain.

Other crystallographic imperfections are etched in a similar manner to that of naturally occurring fission tracks, and these include other charged-particle tracks, defects, dislocations, fluid inclusions, mineral inclusions, polishing scratches, and fractures. Additionally, naturally occurring fission tracks which do not intersect the etched planar surface of an apatite grain may still be etched if they intersect another fission track or a crack in the crystal structure of the apatite grain that does intersect the etched planar surface. In this manner, some subsurface fission tracks can be etched and viewed.

The intersection of the etch pits with the etched planar surface of an apatite grain causes polygonal apertures or etch figures to be formed on that surface. If the crystallographic c-axis of an apatite grain is parallel to the etched planar surface, one of the two orthogonal axes of each etch figure will be parallel to the c-axis of the apatite grain. One of the measurements taken is the maximum diameter of the etch figure taken along a line segment which is parallel to the crystallographic c-axis of the apatite grain. Another measurement taken is the maximum diameter of the etch figure taken along a line segment which is perpendicular to the crystallographic c-axis of the apatite grain. Arithmetic mean maximum etch figure diameters parallel and perpendicular to the crystallographic c-axis are calculated for each apatite grain studied by taking the average of the respective diameters for a series of etch figures measured for each apatite grain.

The mineral apatite is categorized as being fluorine-rich, chlorine-rich, or water-rich apatite, or some combination of these types. By measuring the arithmetic mean maximum diameter parallel to the crystallographic c-axis and the arithmetic mean maximum diameter perpendicular to the c-axis of the etch figures, it is possible to identify the fluorine-rich apatite grains. Etch figures in fluorine-rich apatite tend to be relatively small in size and exhibit a shape characterized as short and narrow. Chlorine-rich apatite tends to exhibit etch figures that are longer and proportionately wider while water-rich apatite etch figures exhibit dimensions which are approximately equal in length to those of chlorine-rich apatite while having a proportionately narrower diameter perpendicular to the crystallographic c-axis.

The crystallographic defects within the apatite crystal or grain that make up a naturally occurring fission track exhibit a natural tendency to convert back to pristine (undamaged) crystalline material. This process is referred to as fission track annealing or annealing and occurs at all temperatures near the Earth's surface. Annealing is the process by which fission tracks are eliminated wholly or partially from their host apatite grain. The annealing process is most rapid at temperatures between 70° C. and 130° C. over geologic time. Annealing occurs more rapidly in fluorine-rich apatite in comparison to the annealing rate in chlorine-rich apatite. Fluorine-rich apatite is most useful for the study of oil formation whereas chlorine-rich apatite is useful for the study of natural gas formation.

Because fluorine-rich apatite occurs most commonly in nature and also because the dimensions and characteristic shape of etch figures formed in fluorine-rich apatite are most easily identified and measured it is desirable to perform analyses on apatite that is predominantly fluorine-rich. However, analyses are also performed on relatively non-fluorine-rich apatite, when such apatite is present, as the present invention provides a method to distinguish between these apatite types. Non-fluorine-rich apatite is apatite that is not categorized as fluorine-rich.

In addition to the measurements of the arithmetic mean maximum etch figure diameters parallel and perpendicular to the crystallographic c-axis for each apatite grain studied, the fission track ages and the perceived track length distributions of fluorine-rich and non-fluorine-rich apatite grains are also measured using presently practiced methods. The etch figure measurements provide a means to group the apatite grains into fluorine-rich apatite and relatively non-fluorine-rich apatite and enable the calculation of a pooled fission track age and a pooled distribution of perceived track lengths corresponding to each apatite type. Furthermore, the etch figure measurements eliminate the need to perform expensive microprobe analyses to determine the chemical composition of the apatite grains.

Fission track age measurements for apatite grains require that the etched apatite grains be masked by a thin sheet of muscovite mica detector and then be placed in close proximity to the core of a nuclear reactor along with a uranium-doped glass covered by a second muscovite mica detector to be irradiated with thermal neutrons in order to determine the amount of $^{238}U$ in the apatite grains. It is presently common practice to irradiate the apatite grains and the muscovite mica detectors prior to measuring the chemical composition of the apatite grains by microprobe analysis. This approach necessarily exposes the analyst to radioactive material but it is practiced because of the high cost of the microprobe analyses and the requirement that all other measurements be completed for the apatite grains prior to microprobe analysis in order to most efficiently employ this method of chemical composition measurement. The method of the present invention eliminates the requirement of prolonged exposure and handling of the radioactive apatite grains after irradiation by permitting a thorough analysis of the chemical composition of the apatite grains to be performed prior to irradiation of the apatite grains in the nuclear reactor. Following irradiation of the apatite grains, it is only necessary to examine the relatively less radioactive muscovite mica detectors that were irradiated in contact with the apatite grains and the uranium-doped glass.

The method of the present invention for performing fission track analysis utilizing the dimensions of etch figures in apatite eliminates the requirement of performing costly microprobe analyses to determine the chemical composition of the apatite grains and in doing so allows more rapid analysis, eliminates the requirement for a high level of expertise at all levels of analyses, and eliminates the need to be exposed to radioactive material for extended periods of time while performing the analyses.

Further features and advantages of the invention will become more readily apparent from the following detailed description when taken in conjunction with the accompanying drawings.

DESCRIPTION OF A PREFERRED EMBODIMENT OF THE METHOD

Figure 1:
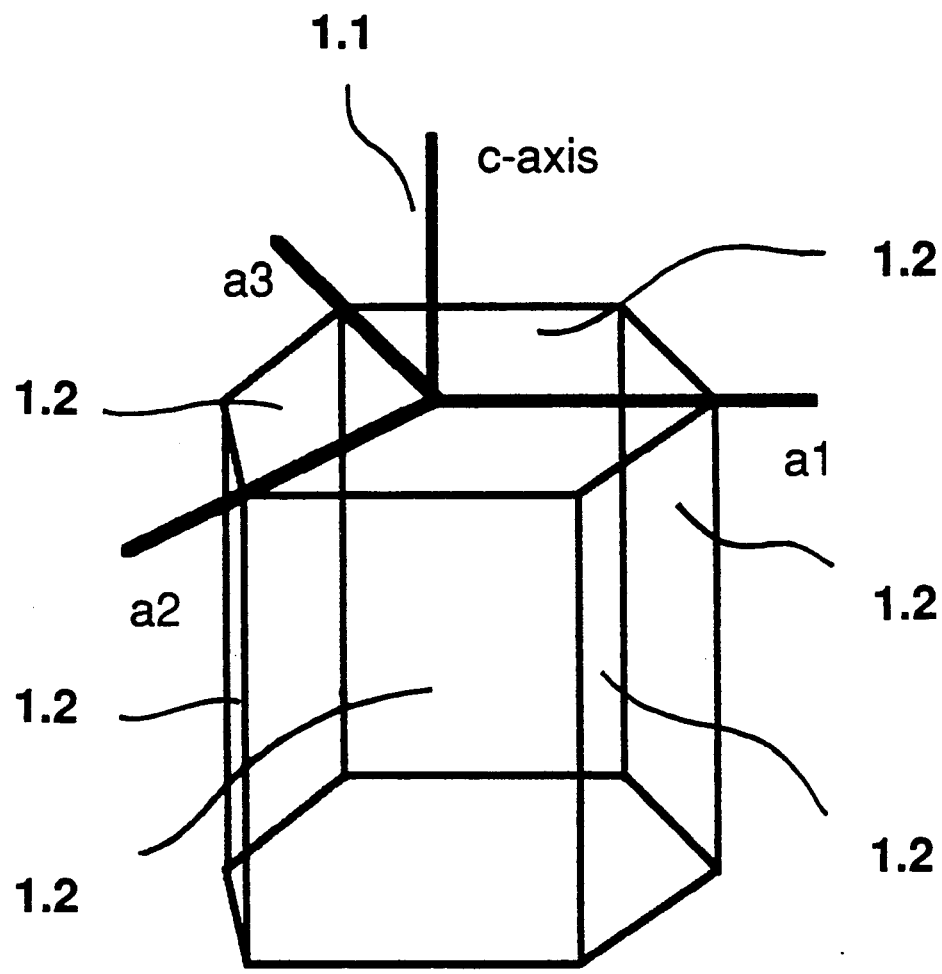
FIG. 1 is a perspective drawing showing relevant features of the crystallographic structure of an apatite crystal.

Apatite is a naturally occurring mineral which exists in many geologic formations in varying quantities. Usually, apatite is found in extremely small quantities as crystals or fragments of crystals within rock formations surrounded by other minerals. Several characteristics of the crystallographic structure of the mineral apatite are illustrated in FIG. 1, including the crystallographic c-axis 1.1 and six of the crystal faces 1.2 that are oriented parallel to the crystallographic c-axis 1.1.

In the exploration for oil and gas it is desirable to accumulate as much data and information as possible regarding the subsurface strata and rock formations which are to be drilled through. These data may include information derived from the constituent apatite grains of the rock which can be analyzed and evaluated to aid in such exploration.

In order to date or determine the approximate date or period of time during which the rock formation was formed, or to otherwise determine relevant characteristics relating to the geological history of the formation, a rock sample is obtained from the bore of a well as it is drilled or from a surface exposure of the rock formation. A sample is taken from a well bore at a desired depth or over a desired depth interval or from a surface exposure at a desired location for purposes of analysis. Samples may be composed of coherent rock pieces, commonly referred to as drill core if from a bore hole, or multiple pieces of rock chips, commonly referred to as well cuttings if from a bore hole.

Figure 2:
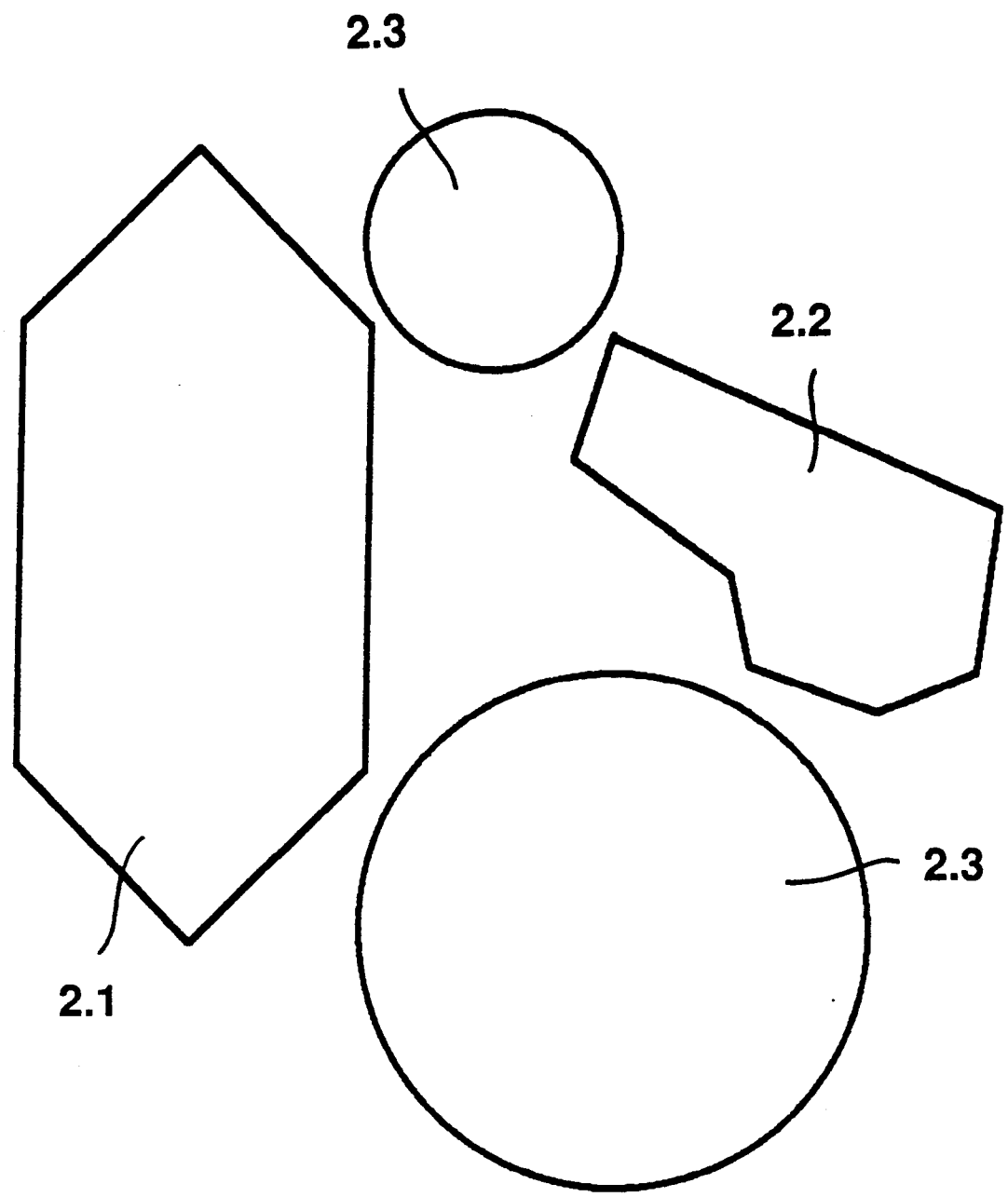
FIG. 2 is an illustration of several apatite grain types.

The sample is then crushed and ground into sand-sized particles or grains, typically 300 micrometers or less across their longest diameter. Referring to FIG. 2, the grains resulting from the crushing and grinding of the rock sample may be whole or complete apatite crystals 2.1, fragments of broken apatite crystals 2.2, abraded apatite crystals or crystal fragments 2.3, other minerals (not shown), or an assemblage of minerals that may or may not include apatite (not shown). Any grain wholly or partly composed of the mineral apatite is called an apatite grain.

The density of the grains is important during the initial stages of the analysis and is instrumental in the separation of apatite grains from the remainder of the rock sample. The density of most rocks and minerals is within the range of 2.50 to 3.00 grams per cubic centimeter while the density of apatite, 3.10 to 3.35 grams per cubic centimeter, is greater than the density of most rocks and minerals.

A first separation step is conducted by immersing the grains of the rock sample in a fluid having a density less than 3.0 grams per cubic centimeter, such as Tribromomethane (or Bromoform) which has a density of 2.89 grams per cubic centimeter. The rock sample grains are typically placed in a container having a stopcock mounted in its bottom. Due to the relative densities of the apatite grains, other grains of rock, and the Tribromomethane, the grains containing the apatite will sink to the bottom of the container along with the grains possessing average densities that exceed 2.89 grams per cubic centimeter which are usually but not always of a ferrous nature. The remaining, lighter or less dense grains will float on the surface of the Tribromomethane. The lighter or less dense grains may be separated from those which possess a higher density than that of the Tribromomethane by skimming or pouring a portion of the immersing liquid from the container. The usual manner in which the relatively dense and light grains are separated is by opening the stopcock on the bottom of the container allowing the more dense grains and a portion of the immersing fluid to drain from the container.

The relatively dense matter containing the apatite grains is then separated from the immersing fluid and cleansed through the use of paper filters and immersion in a cleaning solution such as Acetone (or 2-Propanone). The relatively dense matter usually contains ferrous elements and particles which may have been naturally occurring in the rock sample or may be present due to the fragmentation of the ferrous metallic components of the machinery and equipment used to drill the bore hole, the equipment used to remove the rock sample from the well bore or surface exposure, and other equipment used to crush or grind the sample into sand-sized particles. Examples of such dense matter that remains after the initial separation step along with densities and relative magnetic characteristics are:

| Iron metal | 7.86 grams/cc | extremely magnetic |
|---|---|---|
| Magnetite | 5.20 grams/cc | highly magnetic |
| Zircon | 4.60–4.70 grams/cc | non-magnetic |
| Sphene (titanite) | 3.45–3.55 grams/cc | intermediate magnetic |
| Apatite | 3.10–3.35 grams/cc | non-magnetic | where cc indicates cubic centimeter.

The remaining grains which exhibit the characteristic of greater density than the majority of mineral grains of the rock sample are then separated based upon their magnetic or ferrous characteristics. This is initially done by passing a hand magnet in close proximity to the grains thereby attracting the grains characterized as highly to extremely magnetic. The remaining grains are then placed into a magnetic separator of the type commonly used throughout the geochemical, geophysical, and petrochemical exploration community. An example of such a device is a Frantz Isodynamic Magnetic Separator manufactured by the S.G. Frantz Company, Incorporated. The magnetic separator vibrates the grains to prevent them from clumping together and subjects the grains to an electromagnetic field. Grains that possess greater degrees of magnetic susceptibility are attracted to the electromagnetic field whereas grains with lesser degrees of magnetic susceptibility remain in place. The vibrating apparatus allows the grains possessing greater degrees of magnetic susceptibility to be channeled away from the remaining grains. The grains are subjected to multiple exposures to the electromagnetic field, each successive exposure being of an increased electromagnetic field strength, until the remaining grains include the majority of the apatite and zircon grains.

The remaining grains, containing the majority of the apatite and zircon grains, are then placed in a suitable container and immersed in a fluid having a density less than the density of zircon, such as Diiodomethane (or Methylene Iodide) which possesses a density of 3.33 grams per cubic centimeter. Again, due to the relative densities of the grains and the immersing fluid, the remaining zircon grains settle to the bottom of the container while the remaining apatite grains rise to the surface where they are removed. The resulting component of grains containing apatite is sufficiently pure for purposes of examination.

Figure 3:
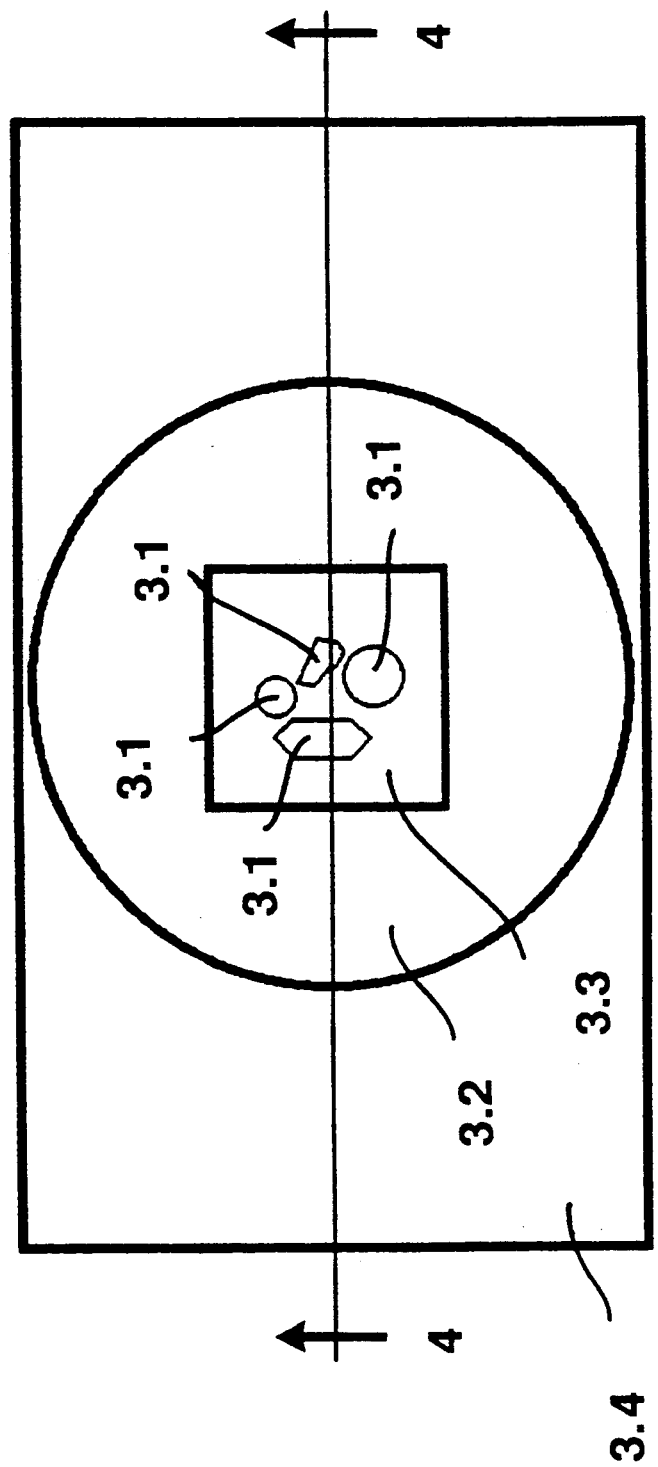
FIG. 3 is a drawing showing the top view of an epoxy wafer containing the apatite grains shown in FIG. 2, attached petrographic slide, and the pouring form.

Referring to FIG. 3, a representative portion of the apatite within an area of approximately 1 square centimeter. The area of the non-stick surface upon which the apatite grains are placed is surrounded on four sides by a form 3.2 that is 1.5 millimeters deep and that is in contact with the planar, non-stick surface. The apatite grains 3.1 are spread evenly over the non-stick surface by hand, within the area defined by the form 3.2, so that they are evenly distributed.

A suitable epoxy resin 3.3 which has been pre-mixed with epoxy hardener is then poured over the apatite grains 3.1 within the area defined by the form 3.2. A petrographic glass microscope slide 3.4 is placed on top of the epoxy resin 3.3 and a slight downward force is applied to ensure that the epoxy resin 3.3 is of uniform thickness and will attach to the petrographic slide 3.4.

The epoxy resin 3.3 is then allowed to harden at room temperature for a period of 24 hours.

Figure 4:
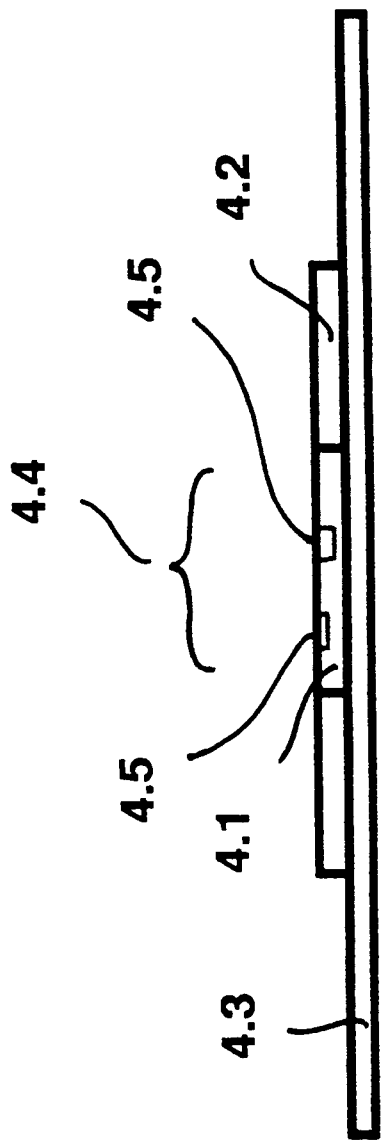
FIG. 4 is a side profile cross-section, through line 4—4 in FIG. 3, of the epoxy wafer containing apatite grains, attached petrographic slide, and the pouring form.

As shown in FIG. 4, the resulting hardened epoxy wafer 4.1 is detached from the non-stick surface and from the form 4.2, remaining attached only to the petrographic slide 4.3. The planar surface 4.4 of the epoxy wafer 4.1 opposite that attached to the petrographic slide 4.3 is then polished to an extremely smooth finish. The polishing of the planar surface 4.4 is accomplished by hand on a polishing lap wheel and results in a minimum thickness of 30 micrometers of the planar surface 4.4 being removed from the epoxy wafer 4.1. As a consequence of removing a minimum of 30 micrometers from the planar surface 4.4 of the epoxy wafer 4.1, a similar thickness of apatite grains 4.5 aligned with and adjacent to the planar surface 4.4 is removed and internal surfaces of the apatite grains 4.5 are exposed.

Figure 5:
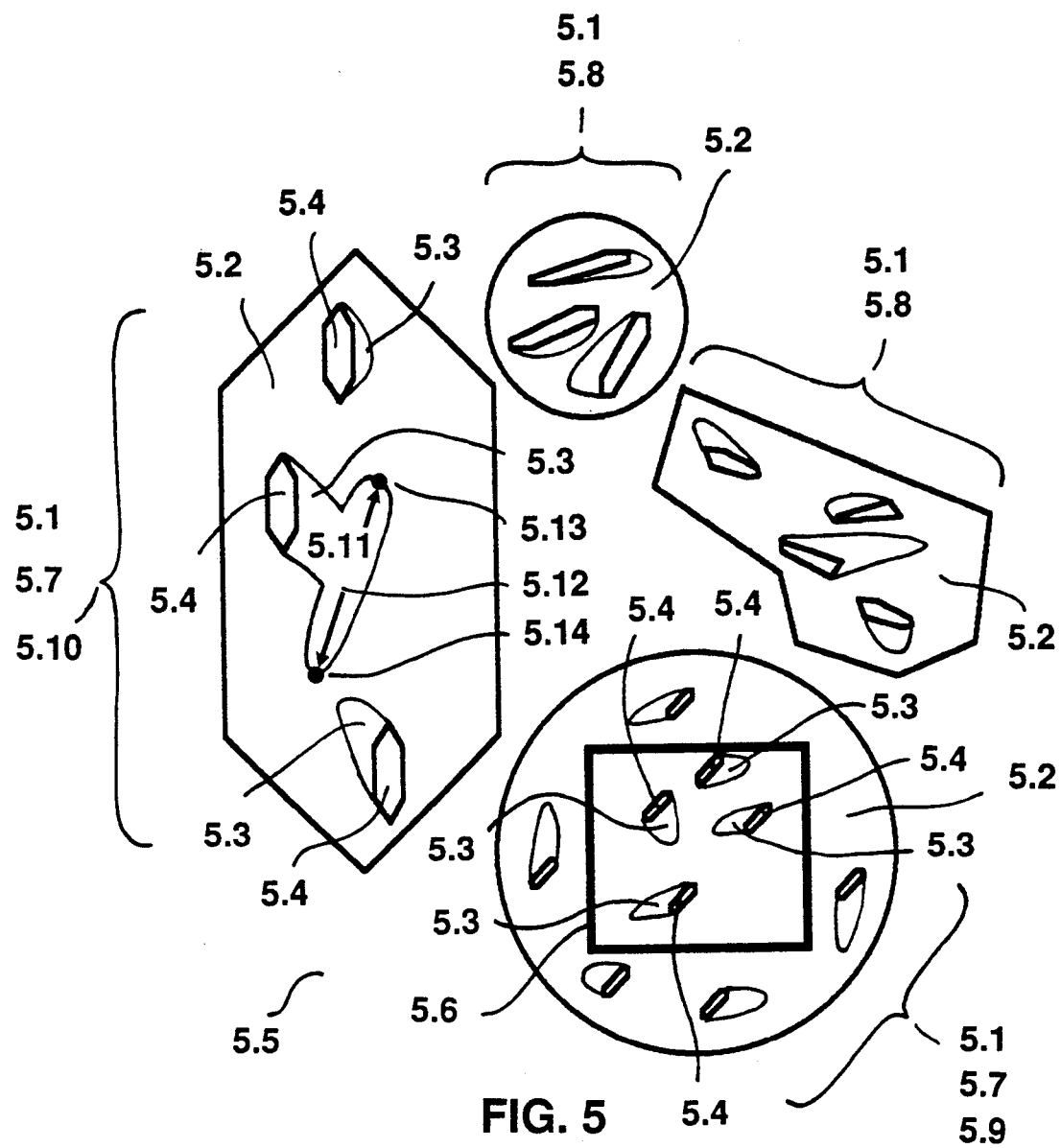
FIG. 5 is an enlarged top view of the polished and etched epoxy wafer containing apatite grains shown in FIG. 3.

Referring to FIG. 5, all naturally occurring apatite grains 5.1 contain trace concentrations of $^{238}U$ (not shown) which periodically and predictably decrease as a result of nuclear decay processes. One method of nuclear decay that affects the $^{238}U$ (not shown) is nuclear fission. Nuclear fission is a decay process whereby the nucleus cleaves into several fragments (not shown) that, once formed, mutually repel one another and tear through the host apatite crystal lattice. Each $^{238}U$ nuclear fission event produces a single, nearly linear zone of crystallographic damage (not shown), called a fission track, in the host apatite grain 5.1. While unetched fission tracks (not shown) cannot be seen optically, they may be enlarged or etched, sufficiently to be viewed using either an optical microscope or a scanning-electron microscope, by exposing the polished planar surface 5.2 of an apatite grain 5.1 to an acidic solution and preferentially dissolving the crystallographic damage that constitutes the naturally occurring fission tracks (not shown). The etching process transforms the fission tracks (not shown) that intersect the etched planar surface 5.2 of an apatite grain 5.1 into etch pits 5.3. An etch pit 5.3 is a polyhedral (or three-dimensional) recess issuing from the etched planar surface 5.2 of the apatite grain 5.1. Prior to becoming an etch pit 5.3, the space within the polyhedral recess was initially composed of apatite material (not shown) that ultimately was preferentially dissolved by the acidic solution. An etch figure 5.4 is the polygonal (or two-dimensional) cross-section of the etch pit 5.3 where it intersects the etched planar surface 5.2 of the apatite grain 5.1. Other crystallographic imperfections (not shown) in the apatite grain 5.1 are etched to create etch pits 5.3 in a similar manner to that of the naturally occurring fission tracks (not shown), and these include other charged-particle tracks, defects, dislocations, fluid inclusions, mineral inclusions, polishing scratches, and fractures.

Referring back to FIG. 4, the epoxy wafer 4.1 and attached petrographic slide 4.3, with the form 4.2 removed, are then immersed in an acid solution (not shown) such as a solution of nitric acid ($HNO_3$) of 5.5 Molar strength at 21 degrees Celsius for 20 seconds while swirling the petrographic slide 4.3 and attached epoxy wafer 4.1 vigorously within the solution to chemically etch the polished apatite grains 4.5 exposed along the planar surface 4.4 of the epoxy wafer 4.1. The etching conditions specified here are selected for the purpose of this application but other variations are possible. The purpose of this treatment with acid solution (not shown) is to chemically etch the planar surface 4.4 of the apatite grains 4.5, and preferentially dissolve apatite matter from within the naturally formed fission tracks (not shown) and other crystallographic imperfections (not shown). Referring to FIG. 5, fission tracks (not shown) and other crystallographic imperfections (not shown) that are preferentially dissolved compared to the remainder of the apatite grain 5.1 and which intersect the etched planar surface 5.2 become etch pits 5.3. The chemical etching procedure reveals the lengths, shapes, and number of etch pits 5.3 for the purpose of analysis. Regardless of the specific etching procedure, it is essential that the same procedure be employed for all epoxy wafers 5.5 for which intercomparisons are to be made.

Referring back to FIG. 4, the petrographic slide 4.3 and attached epoxy wafer 4.1 are then removed from the acid solution (not shown) and washed to remove any remaining traces of acid. The epoxy wafer 4.1 is always washed in distilled water (not shown) to lessen the probability of suspended or dissolved matter (not shown) within the washing solution (not shown) being introduced into the etch pits, 5.3 in FIG. 5, just produced within the apatite grains 4.5. The petrographic slide 4.3 and epoxy wafer 4.1 containing the apatite grains 4.5 are then removed from the washing solution (not shown) and dried sufficiently to remove all fluid from within the etch pits, 5.3 in FIG. 5.

Referring to FIG. 5, in the method of fission track analysis utilizing bulk chemical etching of apatite of the present invention, the epoxy wafer 5.5 containing the apatite grains 5.1 may be viewed using either a binocular optical microscope (not shown) or a scanning-electron microscope (not shown). For purposes of this application, the epoxy wafer 5.5 containing the apatite grains 5.1 is placed under a binocular optical microscope (not shown) of variable magnification power having two illuminating light sources (not shown), a projection tube by which a point source of light (not shown) from a cursor apparatus (not shown) attached to a digitizing tablet (not shown) can be visually observed while looking through the microscope (not shown), and a graticule grid 5.6 located in one of the two eyepieces (not shown) of the binocular optical microscope (not shown). The epoxy wafer 5.5 is oriented such that the polished planar surfaces 5.2 of the apatite grains 5.1 are oriented perpendicular to a beam of light (not shown) that is generated and focused onto the planar surface 5.2 of an apatite grain 5.1, at selected times during the analysis of the epoxy wafer 5.5, from above. This utilization of a light source is referred to as reflected light. Similarly, a beam of light (not shown) is generated from below the epoxy wafer 5.5 and passed through an apatite grain 5.1, at selected times during the analysis of the epoxy wafer 5.5. This utilization of a light source is referred to as transmitted light.

The epoxy wafer 5.5 is viewed utilizing reflected light through the binocular optical microscope (not shown) with the magnification set at 1250X. After the microscope (not shown) has been focused to obtain the clearest image of the etched planar surface 5.2 of each apatite grain 5.1, the apatite grains 5.1 which are of interest are observed. Only a fraction of the apatite grains 5.1 present in the epoxy wafer 5.5 are identified as candidate grains 5.7 for detailed study and measurement of data. Candidate grains 5.7 and are those apatite grains 5.1 which have their crystallographic c-axes, 1.1 in FIG. 1, essentially aligned parallel to their etched planar surfaces 5.2. Non-candidate grains 5.8 are those apatite grains 5.1 which do not have their crystallographic c-axes, 1.1 in FIG. 1, essentially aligned parallel to their etched planar surfaces 5.2; they are not considered candidate grains 5.7 for further study and are disregarded. For a candidate grain 5.7, alignment of the crystallographic c-axis, 1.1 in FIG. 1, with the etched planar surface 5.2 may be verified by utilizing reflected light and verifying that all of the etch FIGS. 5.4 formed by the intersection of etch pits 5.3 with the etched planar surface 5.2 are aligned parallel to one another and that each such etch FIG. 5.4 exhibits an equatorial mirror plane (not shown) oriented perpendicular to the direction of the long axis (not shown) of the etch FIGS. 5.4 and perpendicular to the etched planar surface 5.2. The crystallographic c-axis, 1.1 in FIG. 1, of a candidate grain 5.7 is oriented parallel to the long axis (not shown) of the etch FIGS. 5.4 on its etched planar surface 5.2.

Still referring to FIG. 5, candidate grains 5.7 which are to be selected for fission track age measurement are identified as selected age grains 5.9. Candidate grains 5.7 which are to be selected for perceived track length measurement are identified as selected length grains 5.10. The selected length grains 5.10 may be, but need not be, selected age grains 5.9. Furthermore, the selected length grains 5.10 may be embedded in a polished and etched epoxy wafer (not shown) that is separate and apart from the epoxy wafer 5.5 containing the selected age grains 5.9 for which fission track ages are measured.

Two types of measurements are typically combined for the purpose of determining the thermal history experienced by naturally occurring apatite grains 5.1, the fission track ages of selected age grains 5.9 and the distribution of perceived track lengths in selected length grains 5.10. The fission track age is an indirect indicator of the age of the oldest fission track present in the apatite grains 5.1, and it is used to determine the time interval over which the fission tracks in the in the apatite grains 5.1 have recorded thermal history information. The distribution of perceived track lengths is a direct indicator of the temperature history experienced by the apatite grains 5.1 over said time interval.

Figure 6:
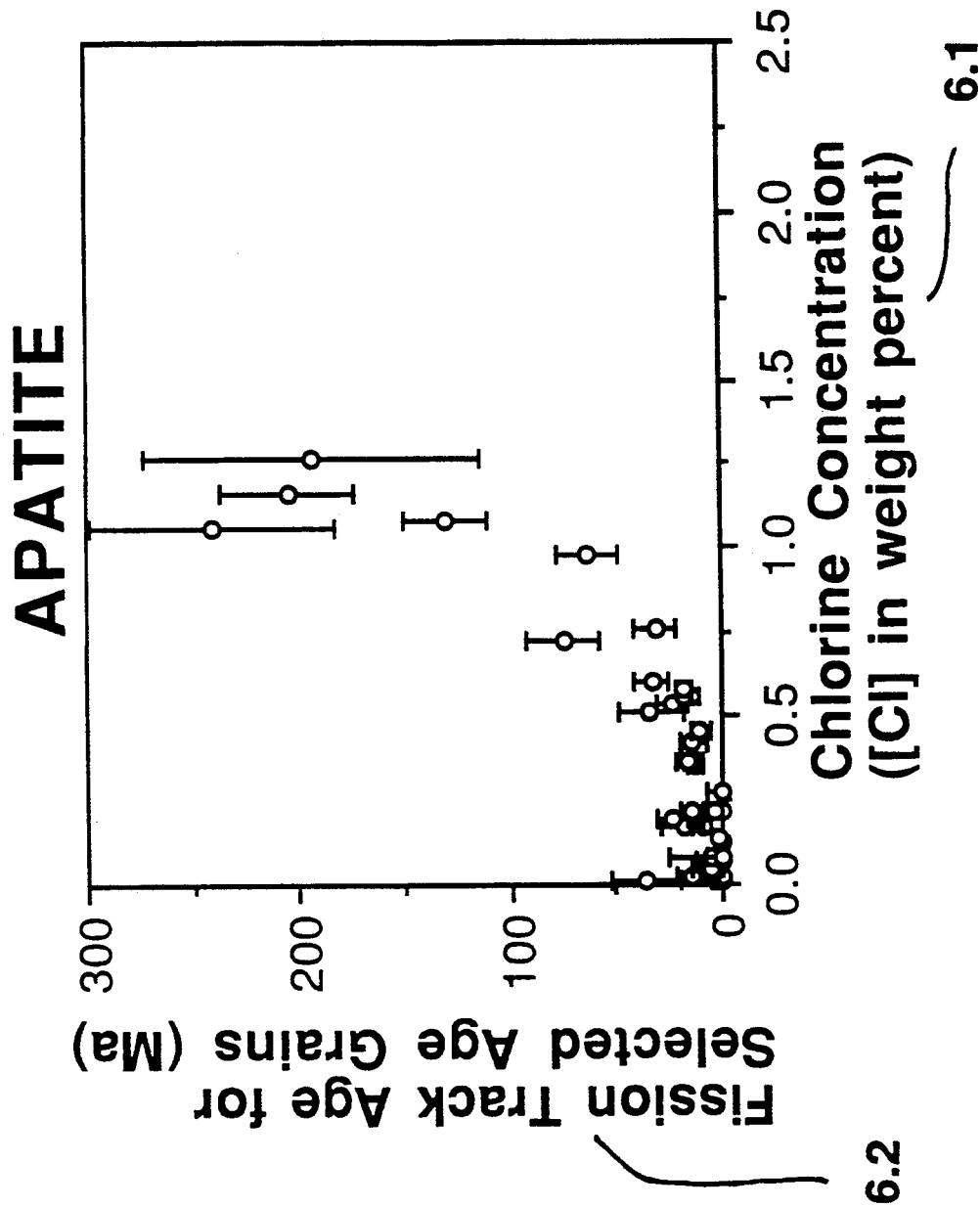
FIG. 6 is a plot of fission track age for selected age grains (in units of Ma where Ma indicates million years) as a function of chlorine concentration (in units of weight percent). The error bars in the vertical direction represent one standard deviation for each fission track age.

The fission track age of a selected age grain 5.9 is essentially proportional to the ratio of the fission tracks per unit volume in a selected volume (not shown) of the selected age grain 5.9 (or daughter product concentration) to the concentration of $^{238}$U nuclei per unit volume (or parent isotope concentration) in same selected volume (not shown) of the same selected age grain 5.9. A fission track age can be calculated for each selected age grain 5.9 studied, or population of selected age grains (not shown), the latter when sufficient evidence exists indicating that each selected age grain 5.9 in the population of age grains (not shown) has similar chemical composition characteristics and has recorded similar geological thermal history information relative to the other selected age grains 5.9 in the population (not shown). However, as illustrated by the example in FIG. 6, the selected age grains, 5.9 in FIG. 5, may exhibit wide ranges in chlorine composition 6.1 (an indicator of chemical composition variation) and fission track ages 6.2 (an indicator of variable thermal histories recorded).

Naturally occurring fission tracks are produced in selected age grains 5.9 and selected length grains 5.10 essentially continuously through time, by virtue of the nature of the $^{238}$U nuclear fission process. Referring back to FIG. 5, the perceived track length 5.11 of an etched, horizontal, wholly confined fission track 5.12, or confined fission track 5.12, within a selected length grain 5.10 is a sensitive indicator of the maximum temperature experienced by the confined fission track 5.12 within the temperature range between 20° C. and 150° C. in rock formations, with the perceived track length 5.11 decreasing with increasing maximum temperature experienced. Consequently, the distribution of perceived track lengths 5.11 in a selected length grain 5.10 or population of length grains (not shown), the latter when sufficient evidence exists indicating that each selected length grain 5.10 in the population of length grains (not shown) has similar chemical composition characteristics and has recorded similar geological thermal history information relative to the other selected length grains 5.10 in the population (not shown), is a sensitive indicator of the total temperature history experienced by the selected length grain 5.10 or population of length grains (not shown) since the time of formation of the oldest fission track present. The distribution (not shown) of perceived track lengths 5.11 is determined by measuring the perceived track lengths 5.11 of a series of randomly encountered confined fission tracks 5.12 in selected length grains 5.10.

Figure 7:
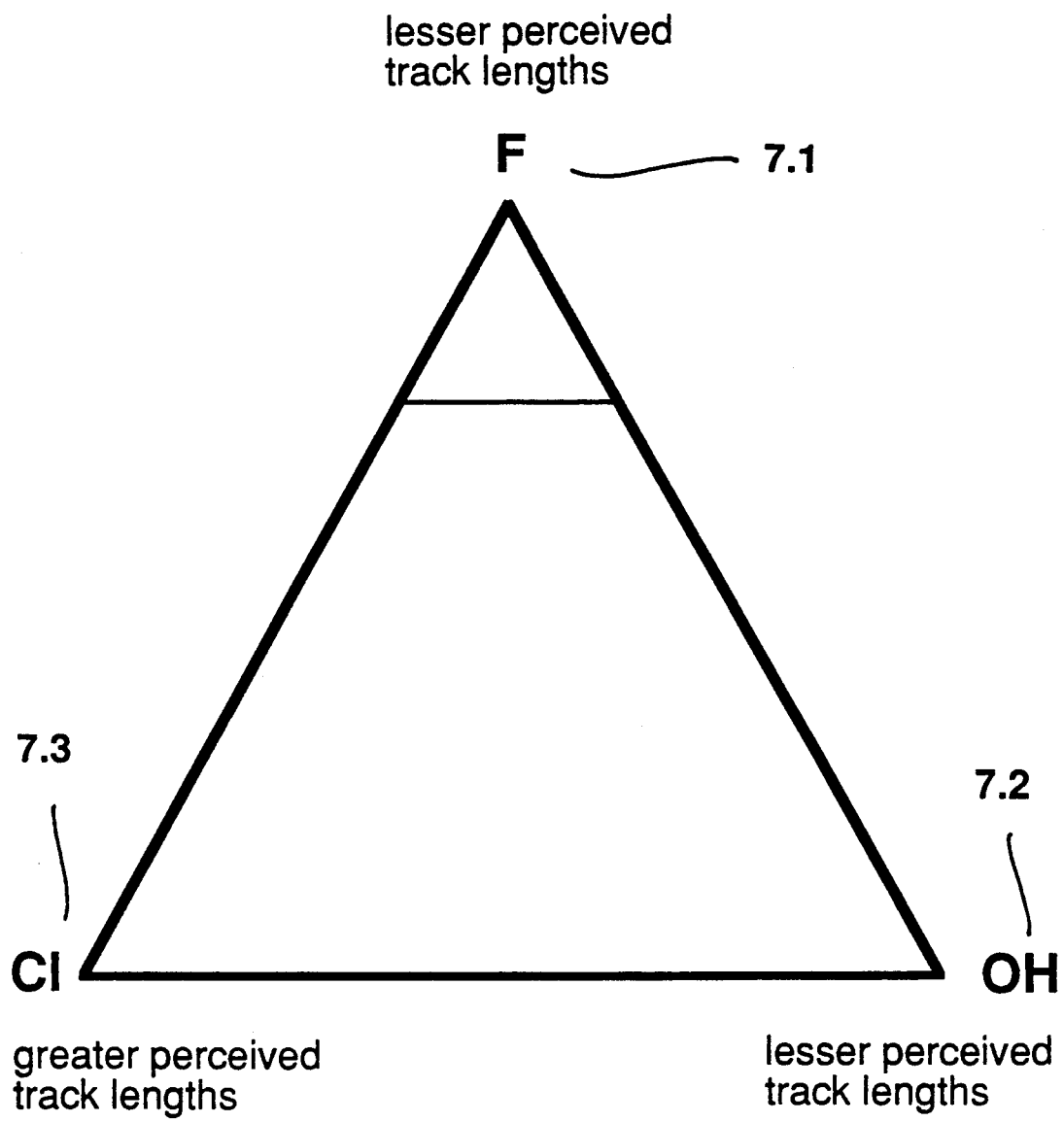
FIG. 7 is a diagram depicting relative perceived track lengths for etched confined fission tracks subjected to the same thermal history in various compositions of apatite.

Referring to FIG. 7, the perceived track length, 5.11 in FIG. 5, is also sensitive to the chemical composition of the selected length grain, 5.10 in FIG. 5, in which it exists, with fission tracks in fluorine-rich selected length grains 7.1 and water-rich selected length grains 7.2 exhibiting lesser perceived track lengths, 5.11 in FIG. 5, than fission tracks in relatively chlorine-rich selected length grains 7.3 subjected to the same maximum temperature. Furthermore, referring to FIG. 8, the dimensions of the etch figures, 5.4 in FIG. 5, in candidate grains, 5.7 if FIG. 5, are sensitive to the chemical composition of the candidate grain, 5.7 in FIG. 5, with fluorine-rich candidate grains 8.1 exhibiting small etch figures, 5.4 in FIG. 5, with large aspect ratios (not shown; the ratio of the arithmetic mean etch figure diameter parallel to the crystallographic c-axis of the candidate grain to the arithmetic mean etch figure diameter perpendicular to the c-axis); water-rich candidate grains 8.2 exhibiting large etch figures, 5.4 in FIG. 5, with large aspect ratios (not shown); and chlorine-rich candidate grains 8.3 exhibiting large etch figures, 5.4 in FIG. 5, with relatively small aspect ratios (not shown).

Referring back to FIG. 5, fission track ages are determined for between 1 and 40 selected age grains 5.9. It is preferable to select age grains 5.9 from the candidate grains 5.7 for which a maximum proportion of the etch pits 5.3 represent etched fission tracks (not shown) and which possess the largest area of etched planar surface 5.2 available for analysis. In order to calculate the fission track age for a selected age grain 5.9 or population of selected age grains (not shown), it is necessary to know the number of naturally occurring fission tracks (not shown), resulting from the spontaneous fission of $^{238}$U (not shown), per unit volume in the selected age grain 5.9 being studied, which is given by the formula:

$$[FT] = P_S/R^{238}$$

where:

[FT], in units of tracks per length cubed, is the number of naturally occurring fission tracks (not shown), resulting from the spontaneous fission decay of $^{238}$U (not shown), per unit volume in the selected age grain 5.9, $P_S$, in units of tracks per length squared, is the surface density of etch FIGS. 5.4, created by the intersection of etch pits 5.3 that represent etched naturally occurring fission tracks (not shown) with the etched planar surface 5.2, on the etched planar surface 5.2 of the selected age grain 5.9; and $R^{238}$, in units of length, is the mean perceived track length 5.11 of naturally occurring fission tracks (not shown) within the apatite grain (not shown), or series of apatite grains (not shown), used to calibrate the fission track ages.

Referring to FIG. 5, the parameter $P_S$ is measured for a selected age grain 5.9, utilizing transmitted light and the binocular optical microscope (not shown) at 1250X, by first bringing the selected age grain 5.9 into sharp focus. The graticule grid 5.6, within one of the two eyepieces (not shown) of the binocular microscope (not shown), is brought into sharp focus along with the selected age grain 5.9 being studied and the selected age grain 5.9 is positioned under a selected portion of the graticule grid 5.6. The selected portion of the graticule grid 5.6, when superimposed upon the image of the selected age grain 5.9 being studied, outlines a portion of the etched planar surface 5.2 having known area. Etch FIGS. 5.4 created by the intersection of etch pits 5.3 representing etched naturally occurring fission tracks (not shown) and the etched planar surface 5.2 within the area outlined by the portion of the graticule grid 5.6 are counted. The naturally occurring fission track density $P_S$, required in the previous equation, is calculated according to the following formula:

$$P_S = N_S / AREA$$

where:

$N_S$, in units of tracks, is the number of etch figures 5.4, created by the intersection of etch pits 5.3 that represent etched naturally occurring fission tracks (not shown) with the etched planar surface 5.2, on the etched planar surface 5.2 of the selected age grain 5.9 within the area outlined by a portion of the graticule grid 5.6; and AREA, in units of length squared, is the area of the etched planar surface 5.2 of the selected age grain 5.9 outlined by a portion of the graticule grid 5.6.

The parameter $R^{238}$ in the earlier equation is the arithmetic mean of a series of perceived track lengths 5.11 measured on 200 randomly encountered confined fission tracks 5.12 in the apatite grain (not shown), or series of apatite grains (not shown), used to calibrate the fission track age measurements. The method employed to accomplish this measurement is described later. Apatite isolated from the Fish Canyon Tuff, San Juan Mountains, Colo. and apatite from the Cerro de Mercado, Durango, Mexico are commonly used to calibrate apatite fission track ages, and therefore constitute age standards. The value of $R^{238}$ that corresponds to a calibration using both of these apatites is approximately 14.50 micrometers.

Figure 9:
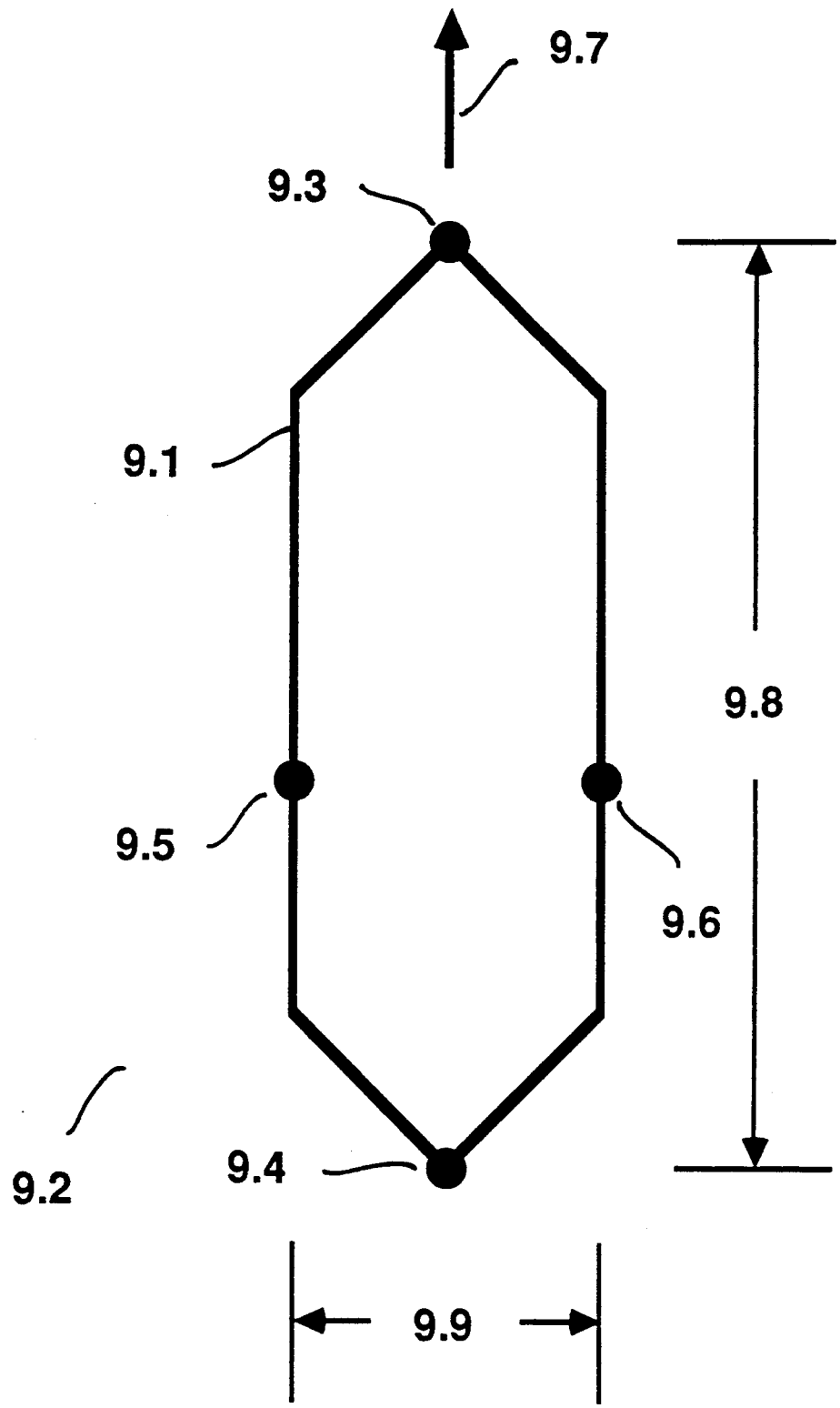
FIG. 9 is an enlarged top view of an etch figure on an etched planar surface of an apatite grain, the surface being parallel to the crystallographic c-axis of the apatite grain.

In accordance with this invention, for each selected age grain 5.9 studied, the chemical composition is determined by measuring the dimensions of the etch FIGS. 5.4 on its etched planar surface 5.2. Referring to FIG. 9, an etch FIG. 9.1 is located and identified on the etched planar surface 9.2 of the selected age grain, 5.9 in FIG. 5, being studied. The locations of 4 points 9.3, 9.4, 9.5, and 9.6 are situated in the field of view (not shown) as seen under the binocular optical microscope (not shown), and are digitized for each of 1 to 5 etch FIGS. 9.1 on the etched planar surface 9.2 of the selected age grain, 5.9 in FIG. 5, for the purpose of determining the arithmetic mean lengths of the two orthogonal diameters 9.7 and 9.8 of the etch FIGS. 9.1. Aligned parallel to the crystallographic c-axis 9.7 of the selected age grain, 5.9 in FIG. 5, is the diameter of the etch FIG. 9.1 parallel 9.8 to the crystallographic c-axis 9.7. Perpendicular to the crystallographic c-axis 9.7 of the selected age grain, 5.9 in FIG. 5, is the diameter of the etch FIG. 9.1 perpendicular 9.9 to the crystallographic c-axis 9.7. Two of the points to be digitized, 9.3 and 9.4, are situated in the field of view in a manner such that the length of the line segment connecting them defines the maximum etch FIG. 9.1 diameter parallel 9.8 to the crystallographic c-axis 9.7. Likewise, the remaining 2 points to be digitized, 9.5 and 9.6, are situated in the field of view in a manner such that the length of the line segment connecting them defines the maximum etch FIG. 9.1 diameter perpendicular 9.9 to the crystallographic c-axis 9.7. Each point is digitized by first superimposing on it the point light source (not shown), viewed through the binocular optical microscope (not shown) and projected from the cursor (not shown) attached to the digitizing tablet (not shown), and then by activating the cursor button (not shown). As each point is digitized, the digitizing tablet (not shown) sends to the computer (not shown) a unique combination of an X coordinate and a Y coordinate, in default units output by the digitizing tablet (not shown). The X and Y coordinates of the locations of the 4 digitized points 9.3, 9.4, 9.5, and 9.6 are $X_1,Y_1$, $X_2,Y_2$, $X_3,Y_3$, and $X_4,Y_4$, respectively. From the coordinates assigned to each point through the digitizing process, the length of the etch FIG. 9.1 diameters, 9.8 and 9.9, are mathematically calculated by the computer (not shown) and stored in a database for further computations. The numerical value $DPAR_i$ of the length of the maximum etch FIG. 9.1 diameter parallel 9.8 to the crystallographic c-axis 9.7 of the i-th (i equals 1 to 5) etch FIG. 9.1 on the etched planar surface 9.2 of the selected age grain, 5.9 in FIG. 5, is determined by the formula:

$$DPAR_i = C\ sqrt((X_2 - X_1)^2 + (Y_2 - Y_1)^2)$$

where:

$DPAR_i$, in units of length, is the numerical value of the length of the maximum etch FIG. 9.1 diameter parallel 9.8 to the crystallographic c-axis 9.7 of the i-th etch FIG. 9.1 on the etched planar surface 9.2 of the selected age grain, 5.9 in FIG. 5, being studied; and C, in units of length, is a scaling factor that converts the units of the digitizing tablet into units of length.

Likewise, the numerical value $DPER_i$ of the length of the maximum etch FIG. 9.1 diameter perpendicular 9.9 to the crystallographic c-axis 9.7 of the i-th (i equals 1 to 5) etch FIG. 9.1 on the etched planar surface 9.2 of the selected age grain, 5.9 in FIG. 5, is determined by the formula:

$$DPER_i = C\ sqrt\ ((X_4 - X_3)^2 + (Y_4 - Y_3)^2)$$

where:

$DPER_i$, in units of length, is the numerical value of the length of the maximum etch FIG. 9.1 diameter perpendicular 9.9 to the crystallographic c-axis 9.7 of the i-th etch FIG. 9.1 on the etched planar surface 9.2 of the selected age grain, 5.9 in FIG. 5, being studied; and C, in units of length, is a scaling factor that converts the units of the digitizing tablet into units of length.

Arithmetic mean values of the maximum etch figure diameter parallel 9.8 to the crystallographic c-axis 9.7 (or DPAR) and the maximum etch figure diameter perpendicular 9.9 to the crystallographic c-axis 9.7 (or DPER) for each selected age grain, 5.9 in FIG. 5, are calculated by summing all of the 1 to 5 values of $DPAR_i$ and $DPER_i$, respectively, and dividing these sums by the number of etch FIGS. 9.1 for which values of $DPAR_i$ and $DPER_i$ were measured.

Referring back to FIG. 5, it is additionally necessary to calculate the perceived track lengths 5.11 of as many as 200 randomly encountered confined fission tracks 5.12 in the selected length grains 5.10. The distribution (not shown) of perceived track lengths 5.11 in the selected length grains 5.10 provides information relevant to the thermal history experienced by the apatite grains 5.1 during their geological evolution. Also, it is necessary to calculate the arithmetic mean of the perceived track lengths 5.11 of 200 randomly encountered confined fission tracks 5.12 in the apatite grain (not shown), or series of apatite grains (not shown), used as age calibration standards; the arithmetic mean of perceived track lengths 5.11 for the age standard, or series of age standards, is the parameter $R^{238}$ that is required in an earlier equation so that the calculation of an apatite fission track age may proceed.

The following procedures are performed on the epoxy wafer 5.5 containing the selected length grains 5.10. These same procedures are repeated on an epoxy wafer (not shown), which may or may not be the same epoxy wafer 5.5 containing the selected length grains 5.10, that contains apatite (not shown) from the age standard, or series of age standards (not shown). Perceived track lengths 5.11 are measured in selected length grains 5.10 for as many as 200 randomly encountered horizontal, confined fission tracks 5.12. Horizontal, confined fission tracks 5.12 are confined fission tracks 5.12 that lie within approximately 10 degrees of parallel to the etched planar surface 5.2 of the selected length grain 5.10, are etched completely to their ends, 5.13 and 5.14, and which ends, 5.13 and 5.14, are confined and clearly visible within the volume of the selected length grain 5.10. The acid solution reaches horizontal, confined fission tracks 5.12 during the chemical etching process by travelling down other etch pits 5.3 or cracks (not shown) that do intersect the planar surface 5.2 of the selected length grain 5.10, and therefore are in direct communication with the etching solution (not shown).

It is necessary to utilize transmitted light in order to locate and focus upon an horizontal, confined fission track 5.12 and view the two opposing ends 5.13 and 5.14 for the purpose of measuring the perceived track length 5.11. Two points, 5.13 and 5.14, situated at opposite ends of the horizontal, confined fission track 5.12 in the field of view as seen under the binocular optical microscope (not shown), are arranged as shown in FIG. 5. The two points to be digitized, 5.13 and 5.14, are situated in the field of view in a manner such that the length of the line segment connecting them defines the perceived track length 5.11 of the confined fission track 5.12 between them. Each point is digitized by first superimposing on it the point light source (not shown), viewed through the binocular optical microscope (not shown) and projected from the cursor (not shown) attached to the digitizing tablet (not shown), and then by activating the cursor button (not shown). As each point is digitized, the digitizing tablet (not shown) sends to the computer (not shown) a unique combination of an X coordinate and a Y coordinate, in the default units output by the digitizing tablet (not shown). The X and Y coordinates of the locations of the two digitized points 5.13 and 5.14 are $X_5,Y_5$ and $X_6,Y_6$, respectively. From the coordinates assigned to each point through the digitizing process, the perceived track length 5.11 of the confined fission track 5.12 is mathematically calculated by the computer (not shown) and stored in a database for further computations. The numerical value TL of the perceived track length 5.11 in the selected length grain 5.10 is determined by the formula:

$$TL = C\ \text{sqrt}((X_6-X_5)^2 + (Y_6-Y_5)^2)$$

where:

TL, in units of length, is the perceived track length 5.11 of an horizontal, confined fission track 5.12 in a selected length grain 5.10; and C, in units of length, is a scaling factor that converts the units of the digitizing tablet into units of length.

Referring again to FIG. 9, arithmetic mean values of the maximum etch figure diameter parallel 9.8 to the crystallographic c-axis 9.7 (or DPAR) and the maximum etch figure diameter perpendicular 9.9 to the crystallographic c-axis 9.7 (or DPER) are determined for each selected length grain, 5.10 in FIG. 5, using the procedures detailed above for the selected age grains, 5.9 in FIG. 5. Similarly, the values of DPAR and DPER for the age calibration standard apatite (not shown) or series of apatites (not shown) are determined to verify the consistency of the etching procedures employed during different etching sessions.

Figure 10:
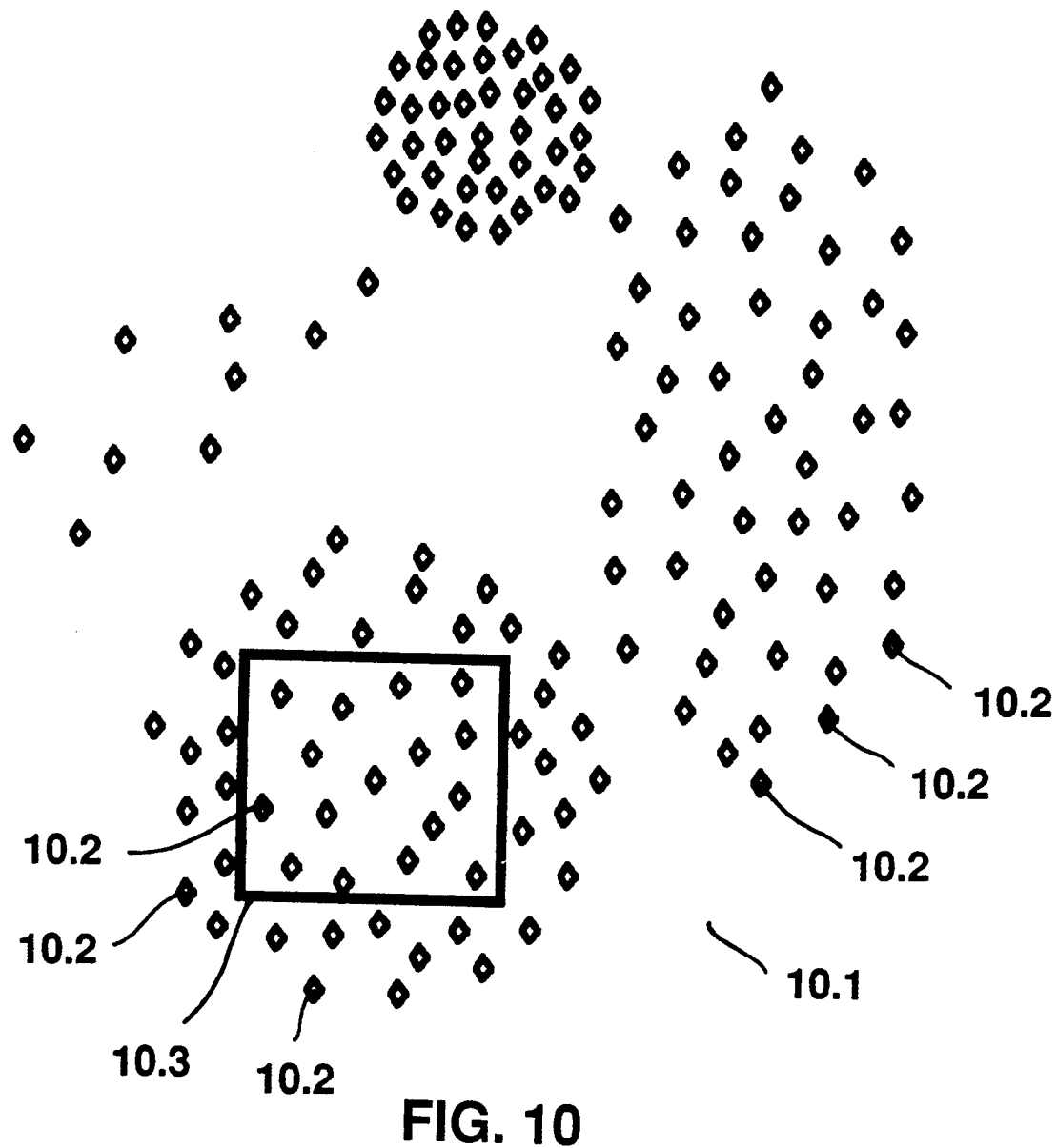
FIG. 10 is an enlarged top view of the etched muscovite mica detector irradiated with thermal neutrons while in contact with the epoxy wafer in FIG. 5.

Referring back to FIG. 5, for the purpose of calculating a fission track age of a selected age grain 5.9, it is necessary to determine the concentration of $^{238}$U within the apatite volume (not shown) immediately below the area of the etched planar surface 5.2 over which the selected portion of the graticule grid 5.6 was placed and for which the naturally occurring fission track density $P_S$ was determined. The volume of apatite of interest (not shown) is the volume of apatite immediately below said area. Referring to FIG. 10 and FIG. 5, in order to accomplish this it is necessary to place a piece of low-uranium (typically less than 1 part per million) muscovite mica 10.1, commonly identified as a solid state nuclear track detector 10.1 or detector 10.1, in intimate contact with the epoxy wafer 5.5, and the etched planar surface 5.5 of each selected age grain 5.9 studied and then place the combination of the epoxy wafer 5.5 and detector 10.1 in close proximity to the core of a nuclear reactor (not shown). Attached to the combination of the epoxy wafer 5.5 and detector 10.1 is a fragment of uranium-doped glass (not shown) that is also covered by a second detector (not shown) in intimate contact with the glass (not shown). An example of a uranium-doped glass (not shown) sufficient for this purpose is Standard Reference Material Number 612 distributed by the National Institute of Standards and Technology.

In selected age grains 5.9, the ratio of the concentration of the uranium isotope $^{238}$U to the concentration of the isotope $^{235}$U is essentially a fixed quantity and a known quantity. The concentration of the uranium isotope $^{235}$U in the uranium-doped glass (not shown) is also a known quantity. Near the core of a nuclear reactor (not shown), the epoxy wafer 5.5 and detector 10.1 combination and the uranium-doped glass (not shown) and second detector (not shown) combination are irradiated with neutrons (not shown) possessing a distribution of energies dominated by low energies. Neutrons of this type are called thermal neutrons. It is preferred that the epoxy wafer 5.5 and detector 10.1 combination and the uranium-doped glass (not shown) and second detector (not shown) combination be exposed to a thermal neutron dose of approximately $1 \times 10^{16}$ neutrons per centimeter squared. The nucleus of the uranium isotope $^{235}U$ possesses a large cross-section for thermal neutron capture, and when an $^{235}U$ nucleus captures a thermal neutron it cleaves into fragment nuclei (not shown), a process called induced fission, and the fission fragment nuclei (not shown) tear through their host material in a manner virtually identical to that described for the spontaneous fission of the isotope $^{238}U$. The number of induced fission events that occurs in an apatite volume of interest (not shown) of a selected age grain 5.9 is proportional to the concentration of $^{235}U$, and the concentration of $^{238}U$. Likewise, the number of induced fission events that occurs in the uranium-doped glass (not shown) is proportional to the known concentration of $^{235}U$ in the glass (not shown).

When an $^{235}U$ nucleus experiences induced fission in a selected age grain 5.9 within the apatite volume of interest (not shown), one of its resultant fragment nuclei (not shown) possesses a predictable probability of passing out of the selected age grain 5.9, whereupon it hits the detector 10.1 in contact with the planar surface 5.2 within the area originally outlined by the graticule grid 5.6. Likewise, one of the resultant nuclei (not shown) from the induced fission of an $^{235}U$ nucleus in the uranium-doped glass (not shown) possesses a predictable probability of passing out of the uranium-doped glass (not shown), whereupon it hits the second detector (not shown) in contact with the uranium-doped glass (not shown).

After irradiating the epoxy wafer 5.5 and detector 10.1 combination and the uranium-doped glass (not shown) and second detector (not shown) combination, they are removed from the nuclear reactor (not shown) and the detector 10.1 is separated from the epoxy wafer 5.5. Similarly, the second detector (not shown) is separated from the uranium-doped glass (not shown). The detectors 10.1 are chemically etched, for the purpose of preferentially dissolving the matter that constitutes the induced fission tracks (not shown) implanted into them during the thermal neutron irradiation process, thereby creating induced fission track etch pits 10.2 issuing from the planar surface (not shown) of the detectors 10.1, by placing them in a 48% hydrofluoric acid (HF) solution (not shown) for 13 minutes at 24° C. The time of exposure of the detectors 10.1 to the hydrofluoric acid solution (not shown) is inversely proportional to the temperature, and may be longer or shorter depending upon the temperature at the time.

The $^{238}U$ concentration in an apatite volume of interest (not shown) in a selected age grain 5.9 is calculated according to the following formula:

$$[^{238}U] = 137.88 \ [^{235}U_g] \ (R_g R_a) \ (P_{ia}/P_{ig})$$

where:

$[^{238}U]$, in units of nuclei per length cubed, is the concentration of the uranium isotope $^{238}U$ in a selected age grain 5.9 within the apatite volume of interest (not shown), 137.88, in units of nuclei per nuclei, is a constant for all selected age grains 5.9 which represents the naturally occurring concentration ratio of the uranium isotopes $^{238}U$ to $^{235}U$, $[^{235}U_g]$, in units of nuclei per length cubed, is the concentration of the uranium isotope $^{235}U$ in the uranium-doped glass (not shown), $R_g$, in units of length, is the average distance travelled by a single fission fragment nucleus (not shown) in the uranium-doped glass (not shown), $R_a$, in units of length, is the average distance travelled by a single fission fragment nucleus (not shown) in the selected age grain 5.9, $P_{ia}$, in units of tracks per length squared, is the surface density of induced fission track etch pits 10.2 that cross the etched planar surface (not shown) of the detector 10.1 within the area of the detector 10.1 outlined by the graticule grid 10.3 that was in intimate contact with the previously studied area, outlined by the graticule grid 5.6 in FIG. 5, of the selected age grain 5.9, and $P_{ig}$, in units of tracks per length squared, is the surface density of induced fission track etch pits (not shown) that cross the etched planar surface (not shown) of the detector (not shown) that was in intimate contact with the uranium-doped glass (not shown).

The parameter $P_{ia}$ is measured for a selected age grain 5.9, utilizing transmitted or reflected light and the binocular optical microscope (not shown) at 1250X, by first bringing the detector 10.1 into sharp focus. The graticule grid 10.3, within one of the two eyepieces (not shown) of the binocular optical microscope (not shown), is brought into sharp focus along with the detector 10.1, and the area of the detector 10.1 that was in intimate contact with a selected age grain 5.9 is located. The portion of the detector 10.1 area that was in contact with the portion of the etched planar surface 5.2 of the selected age grain 5.9 that had been previously outlined by a selected portion of the graticule grid 5.6, is itself outlined by a selected portion of the graticule grid 10.3 having the same area as the selected portion of the graticule grid 5.6 used on the selected age grain 5.9. The number of induced fission track etch pits 10.2 that intersect the etched planar surface (not shown) of the detector 10.1 within the area outlined by the portion of the graticule grid 10.3 are counted. The induced fission track density $P_{ia}$ for the selected age grain 5.9 is calculated according to the following formula:

$$P_{ia} = N_i / AREA$$

where:

$N_i$, in units of tracks, is the number of induced fission track etch pits 10.2, resulting from the induced fission of $^{235}U$, that intersect the planar surface (not shown) of the detector 10.1 within the area of the detector 10.1 outlined by a portion of the graticule grid 10.3, the portion of the detector 10.1 within the outlined area having been in contact with the previously studied area of a selected age grain 5.9 that had been outlined by a selected portion of the graticule grid 5.6; and AREA, in units of length squared, is the area of the surface of the detector 10.1 outlined by the portion of the graticule grid 10.3 and is equal in area to the portion of the etched planar surface 5.2 of the selected age grain 5.9 that had been outlined by a selected portion of the graticule grid 5.6.

The parameter $P_{ig}$ is measured for the uranium-doped glass (not shown) in a manner similar to that employed to measured $P_{ia}$. The second detector (not shown) from the uranium-doped glass (not shown) is placed under the binocular optical microscope (not shown) at 1250X magnification, reflected light is utilized, and the detector (not shown) is brought into sharp focus. A selected portion of the graticule grid (not shown), within one of the two eyepieces (not shown) of the binocular optical microscope (not shown), is brought into sharp focus along with the second detector (not shown), and the area (not shown) of the second detector (not shown) that was in intimate contact with the uranium-doped glass (not shown) is located. A selected portion of the second detector (not shown) is outlined by a portion of the graticule grid (not shown) having known area as previously described. The number of induced fission track etch pits (not shown) that intersect the etched planar surface (not shown) of the second detector (not shown) within the area outlined by the portion of the graticule grid (not shown) is counted. This counting procedure is repeated for new portions (not shown) of the etched planar surface (not shown) of the second detector (not shown) until a combined total of 2000 or more induced fission track etch pits (not shown) are counted. The induced fission track density $P_{ig}$ is calculated according to the following formula:

$$P_{ig} = N_g / AREA_g$$

where:

$N_g$, in units of tracks, is the number of induced fission track etch pits (not shown), resulting from the induced fission of $^{235}U$, that intersect the etched planar surface (not shown) of the second detector (not shown) within the sum of the individual portions (not shown) of the second detector (not shown) outlined by portions of the graticule grid (not shown), the portions of the second detector (not shown) having been in contact with the uranium-doped glass (not shown); and $AREA_g$, in units of length squared, is the sum of the individual portions (not shown) of the etched planar surface (not shown) of the second detector (not shown) over which induced fission track etch pits (not shown) were counted.

Upon determination of the number of fission tracks per unit volume ([FT]) and concentration of $^{238}U$ ([$^{238}U$]) for a volume of interest (not shown) of a selected age grain 5.9, the fission track age may be calculated for the selected age grain 5.9. The fission track age T is calculated using the formula:

$$T = (1/l_D) \ln((l_D/l_F)([FT]/[^{238}U]) + 1)$$

where:

T, in units of millions of years, is the fission track age for the selected age grain 5.9, $l_D$, in units of nuclei per million years, is the total decay constant for $^{238}U$, $l_F$, in units of nuclei per million years, is the fission decay constant for $^{238}U$,

[FT], in units of tracks per length cubed, is the number of naturally occurring fission tracks (not shown), resulting from the spontaneous fission decay of $^{238}U$ (not shown), per unit volume in a volume of interest (not shown) in the selected age grain 5.9, and;

[$^{238}U$], in units of nuclei per length cubed, is the concentration of the uranium isotope in the selected age grain 5.9 within the apatite volume of interest (not shown).

Figure 8:
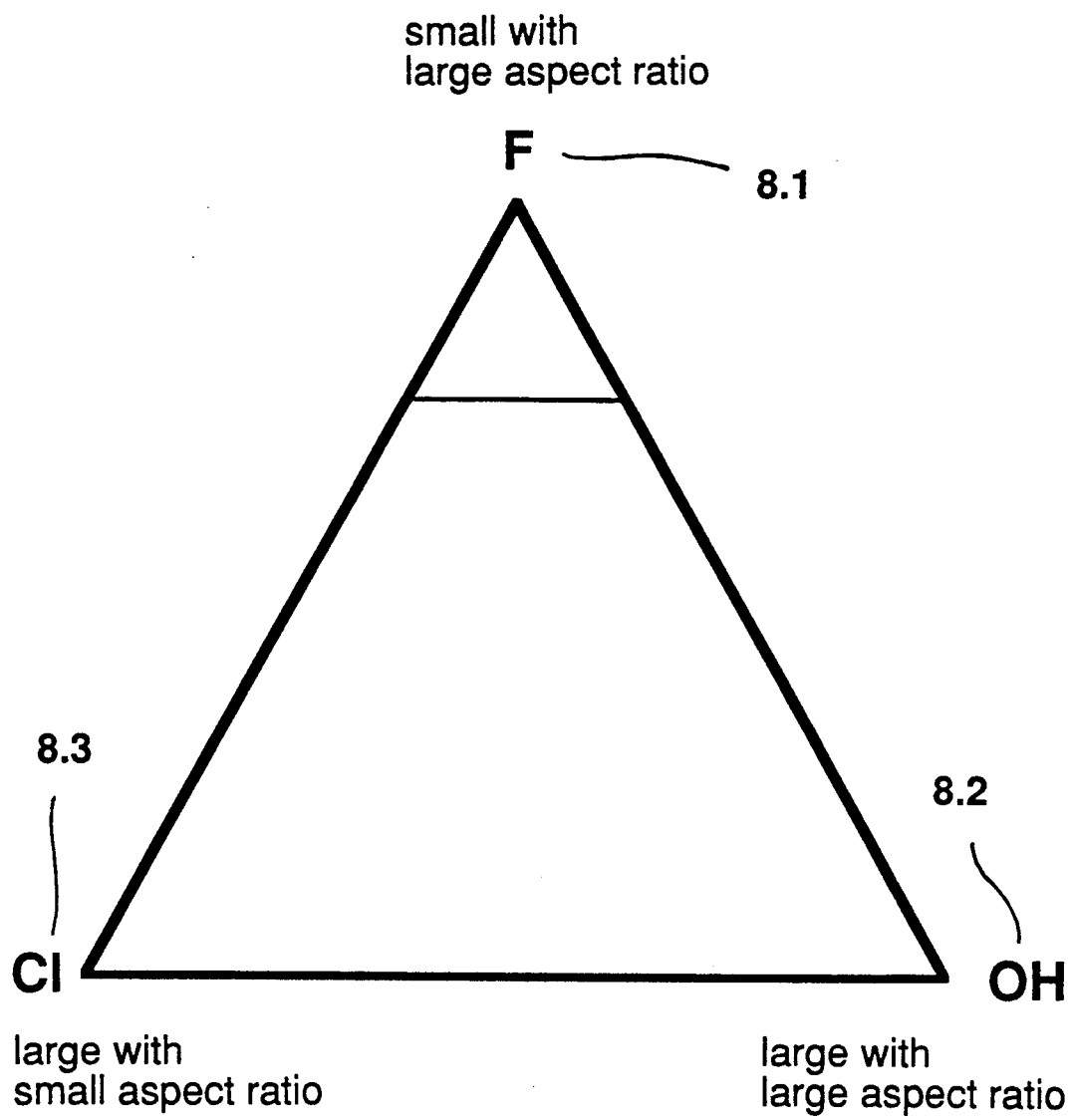
FIG. 8 is a diagram depicting relative etch figure dimensions (maximum diameters parallel and perpendicular to the crystallographic c-axis of the host candidate grain) and aspect ratios (ratio of the maximum diameter parallel versus perpendicular to the crystallographic c-axis) for various compositions of apatite subjected to the same etching procedures.

The present invention relates to the characterization of the chemical composition of selected age grains 5.9 and selected length grains 5.10 using the dimensions of etch FIGS. 5.4. To accomplish the task of the characterization of the chemical composition of selected age grains 5.9 and selected length grains 5.10, etch FIGS. 5.4 are identified which exhibit dimensions characteristic of the apatite composition, as illustrated in FIG. 8. An etch FIG. 5.4 is the polygonal (or two-dimensional) cross-section of the etch pit 5.3 where it intersects the etched planar surface 5.2 of the selected age grain 5.9 or selected length grain 5.10. The crystallographic imperfections (not shown) in a candidate apatite grain 5.7 that are etched to created etch pits 5.3 that form etch FIGS. 5.4 on the etched planar surfaces 5.2 include naturally occurring fission tracks, other charged-particle tracks, defects, dislocations, fluid inclusions, mineral inclusions, polishing scratches, and fractures. Numerous apparatus may be utilized to accomplish this task of apatite chemical composition determination using etch FIG. 5.4 dimension measurements including some combination of an binocular optical microscope (not shown), a digitizing tablet (not shown), a video camera (not shown), a photographic camera (not shown), a computerized image analysis system (not shown), and a scanningelectron microscope (not shown). The following discussion emphasizes etch FIGS. 5.4 measured using a combination of a binocular optical microscope (not shown) and a digitizing tablet (not shown).

The equipment used to conduct etch FIG. 5.4 diameter measurement operations is common throughout the geological research community and can be readily obtained. The basic equipment required comprises a binocular optical microscope (not shown), a personal computer (not shown), an illuminated cursor apparatus (not shown) and digitizing tablet (not shown), interface board (not shown), interfacing software (not shown), and the projection tube mechanism (not shown) by which the light (not shown) emanating from the cursor (not shown) can be superimposed upon the magnified view of the selected age grains 5.9 and selected length grains 5.10.

Due to the nature and level of the ionizing radiation emitted by the matter that constitutes the epoxy wafer 5.5 containing the apatite grains 5.1 after irradiation with thermal neutrons, it is desirable to perform the etching and corresponding measurements on the epoxy wafer 5.5 prior to placing it in close proximity to the nuclear reactor core (not shown) to be irradiated. Prior to the present invention, it has been common practice to study the selected age grains 5.9 and the selected length grains 5.10 after the epoxy wafer 5.5 had been irradiated with thermal neutrons. The method of the present invention allows the measurements that must be made directly on the selected age grains 5.9 and selected length grains 5.10 to be performed prior to the irradiation procedure; only the detectors 10.1 require study after irradiation.

The detectors 10.1 emit much less radiation than the epoxy wafer 5.5 containing the apatite grains 5.1 after the irradiation procedure. Additionally, the radiation levels of the detectors 10.1 recede below the levels promulgated by the Nuclear Regulatory Commission as requiring a license to receive and to possess, and those with which the Inventor is personally familiar, within one to three weeks while the epoxy wafer 5.5 continues to exceed such standards for a considerably longer period of time. The standards which are applicable are set forth in the Texas Regulations For Radiation Control published by the Bureau of Radiation Control of the Texas Department of Health. Such standards are set forth in Part 41 (a) for exempt concentrations of radioactivity, Part 41 (b) for exempt quantities of radioactivity, and Appendices 41-A and 41-B.

Figure 11:
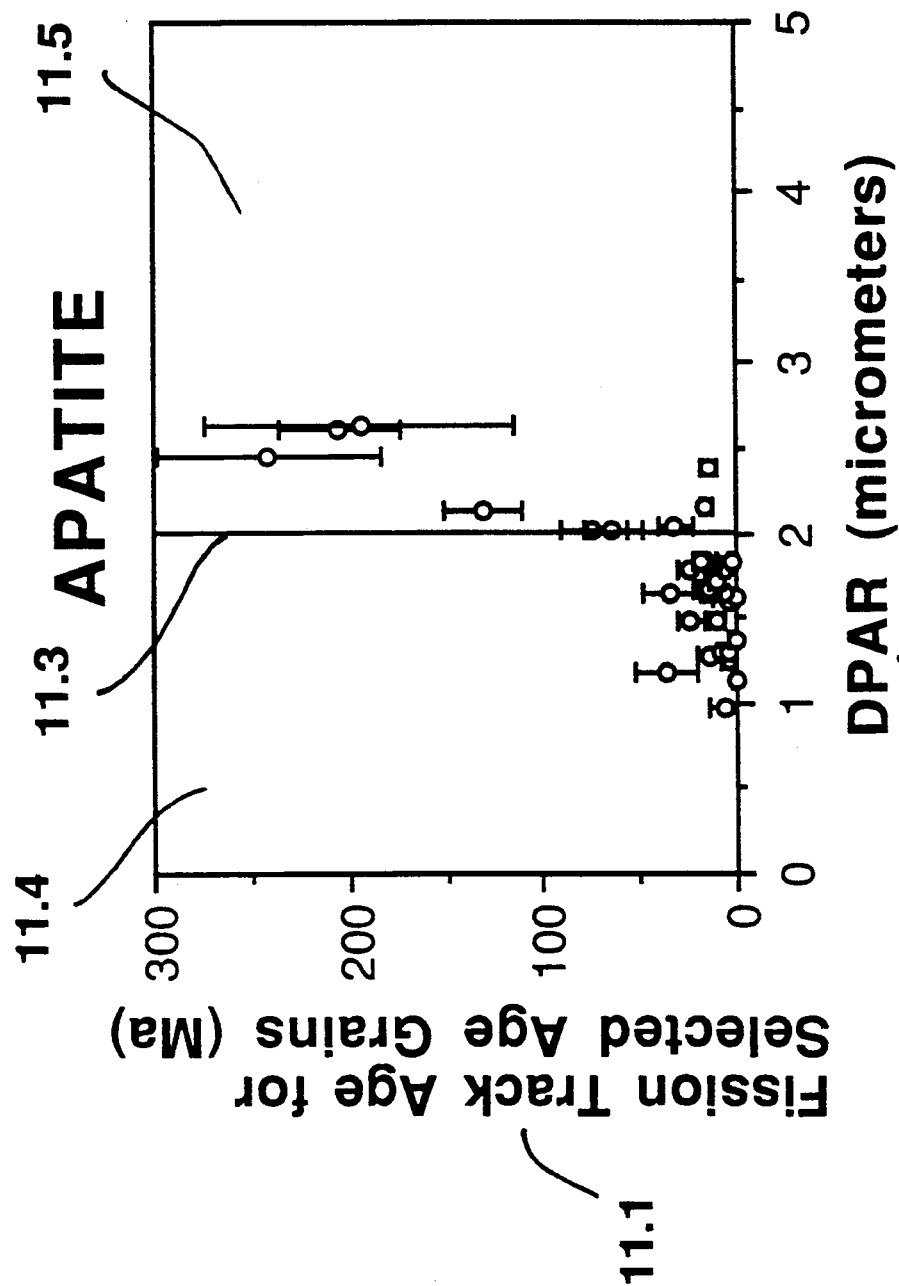
FIG. 11 is a plot of fission track age for selected age grains (in units of Ma where Ma indicates million years) as a function of the arithmetic mean maximum etch figure diameter parallel to the crystallographic c-axis, DPAR (in units of micrometers). The error bars in the vertical direction represent one standard deviation for each fission track age.

Referring to FIG. 11, after all of the measurements and calculations are completed, in order to accurately interpret the accumulated data it is necessary to plot the fission track ages 11.1 (or T) for the selected age grains 5.9 taken as a function of DPAR 11.2 (or the mean maximum etch FIG. 5.4 diameter parallel 9.8 to the crystallographic c-axis 9.7). The plot in FIG. 11 is similar to the plot in FIG. 6, except that the abscissa in FIG. 11 is DPAR 11.2 instead of chlorine concentration 6.1.

Figure 12:
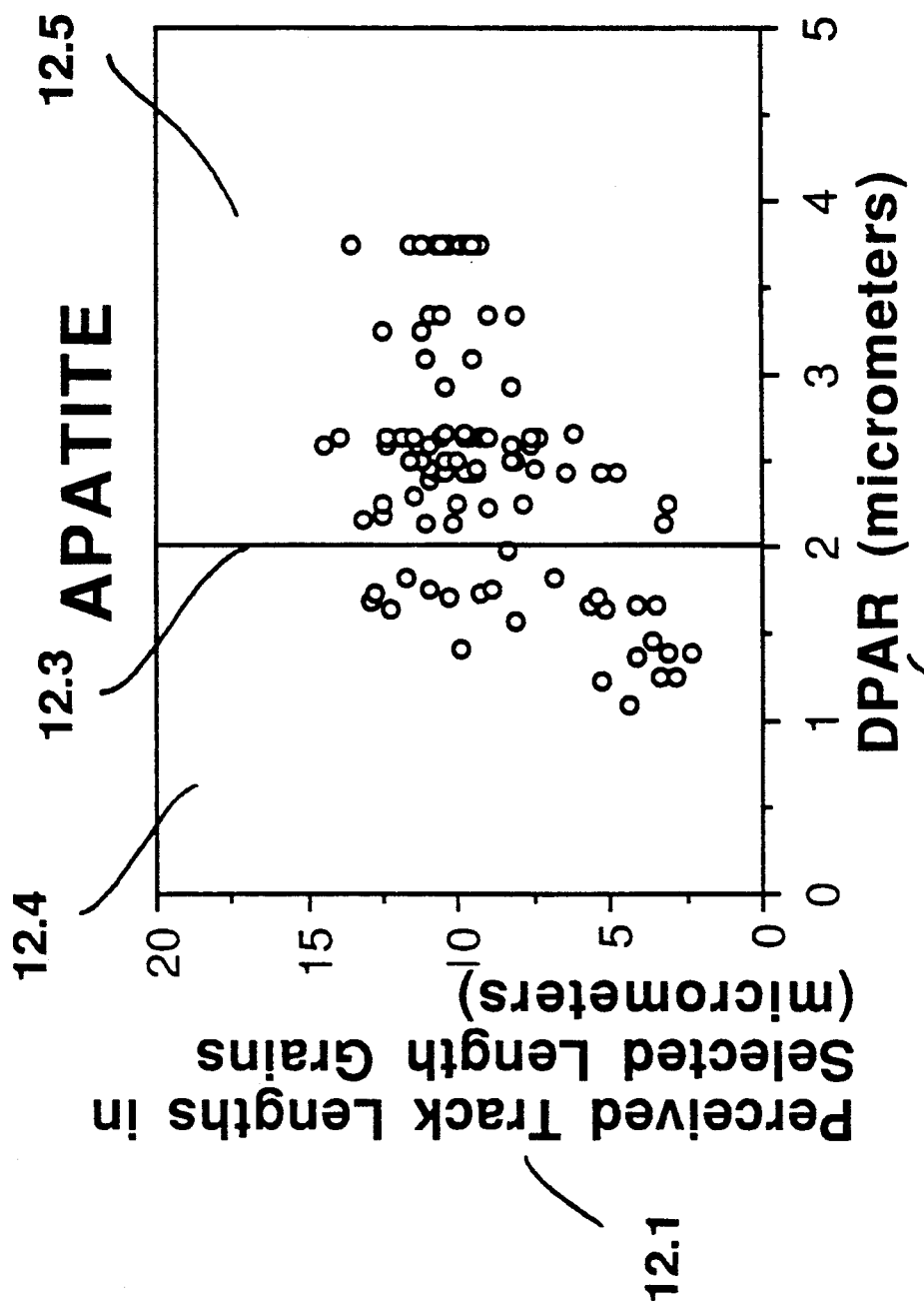
FIG. 12 is a plot of perceived track length in selected length grains (in units of micrometers) as a function of the arithmetic mean maximum etch figure diameter parallel to the crystallographic c-axis, DPAR (in units of micrometers).

Referring to FIG. 12, it is also necessary to plot the perceived track lengths 12.1 (or TL) in the selected length grains 5.10 taken as a function of DPAR 12.2 (or the mean maximum etch FIG. 5.4 diameter parallel 9.8 to the crystallographic c-axis 9.7). No complementary plot of perceived track length 12.1 taken as a function of chlorine concentration 6.1 is offered here due to the great expense in terms of time, money, and expertise required to determine chlorine concentration values 6.1, using an electron microprobe, for all of the selected length grains 5.10 for which perceived track lengths 12.1 were measured.

Mean maximum etch FIG. 5.4 diameters parallel 9.8 and perpendicular 9.9 to the crystallographic c-axis 9.7 are easily and inexpensively measured for both the selected age grains 5.9 and selected length grains 5.10. On the other hand, microprobe data are only rarely obtained for each of the selected age grains 5.9 and each of the selected length grains 5.10. Furthermore, etch FIG. 5.4 diameter 9.8 and 9.9 measurements can be made on the selected age grains 5.9 prior to irradiation of the epoxy wafer 5.5 with thermal neutrons, thereby substantially lowering the health risks of making the measurements, and they require no additional capital investment in equipment or expertise.

Figure 13:
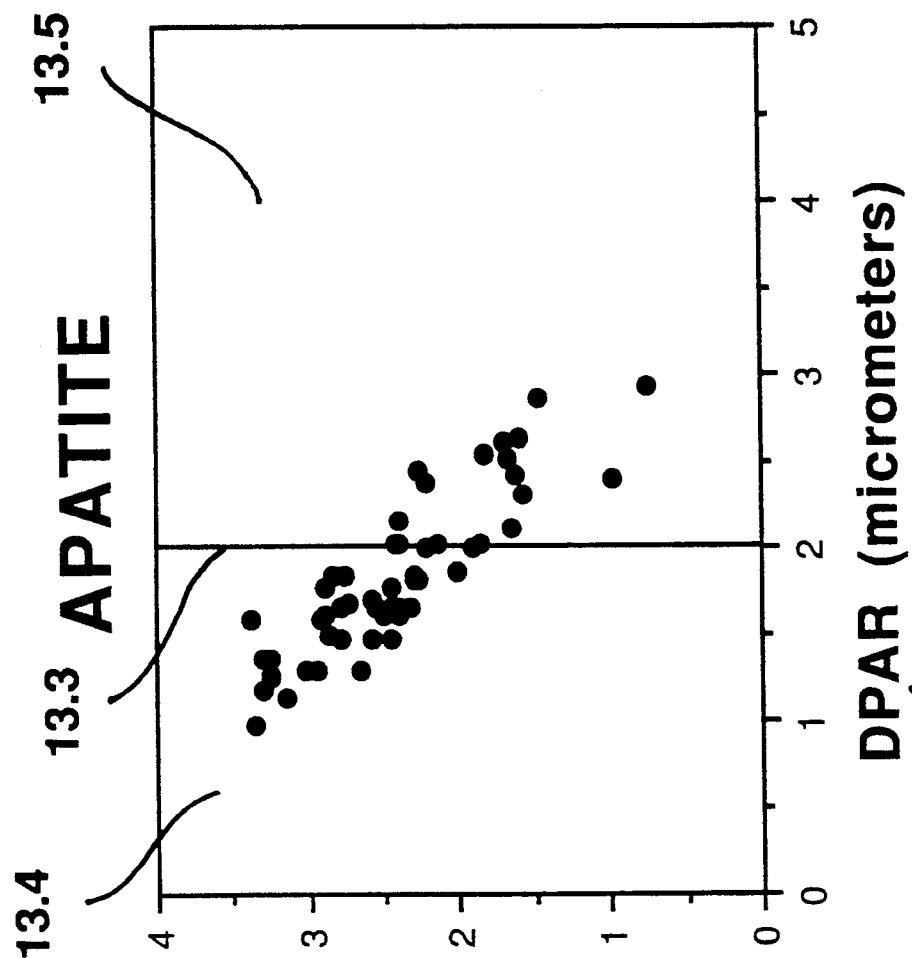
FIG. 13 is a plot of fluorine concentration [F] (in units of weight percent) of selected age grains and a fraction of the selected length grains from FIGS. 11 and 12 as a function of the arithmetic mean maximum etch figure diameter parallel to the crystallographic c-axis, DPAR (in units of micrometers).
Figure 14:
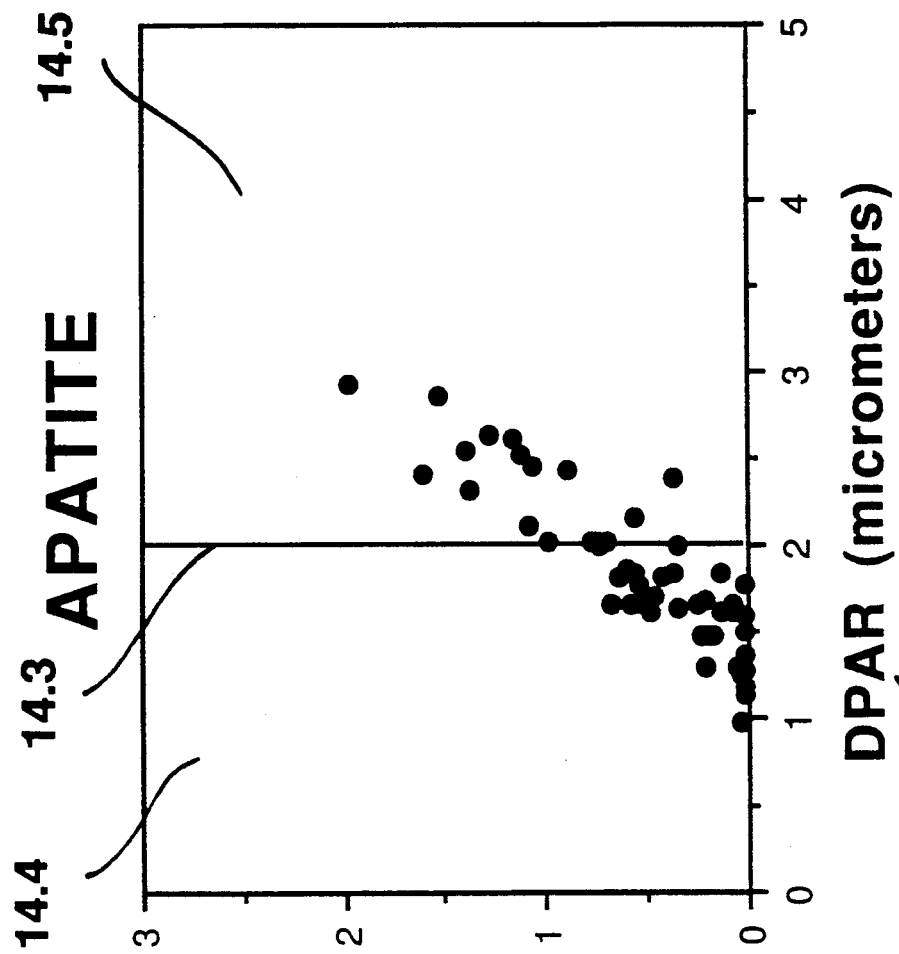
FIG. 14 is a plot of chlorine concentration [Cl] (in units of weight percent) of selected age grains and a fraction of the selected length grains from FIGS. 11 and 12 as a function of the arithmetic mean maximum etch figure diameter parallel to the crystallographic c-axis, DPAR (in units of micrometers).
Figure 15:
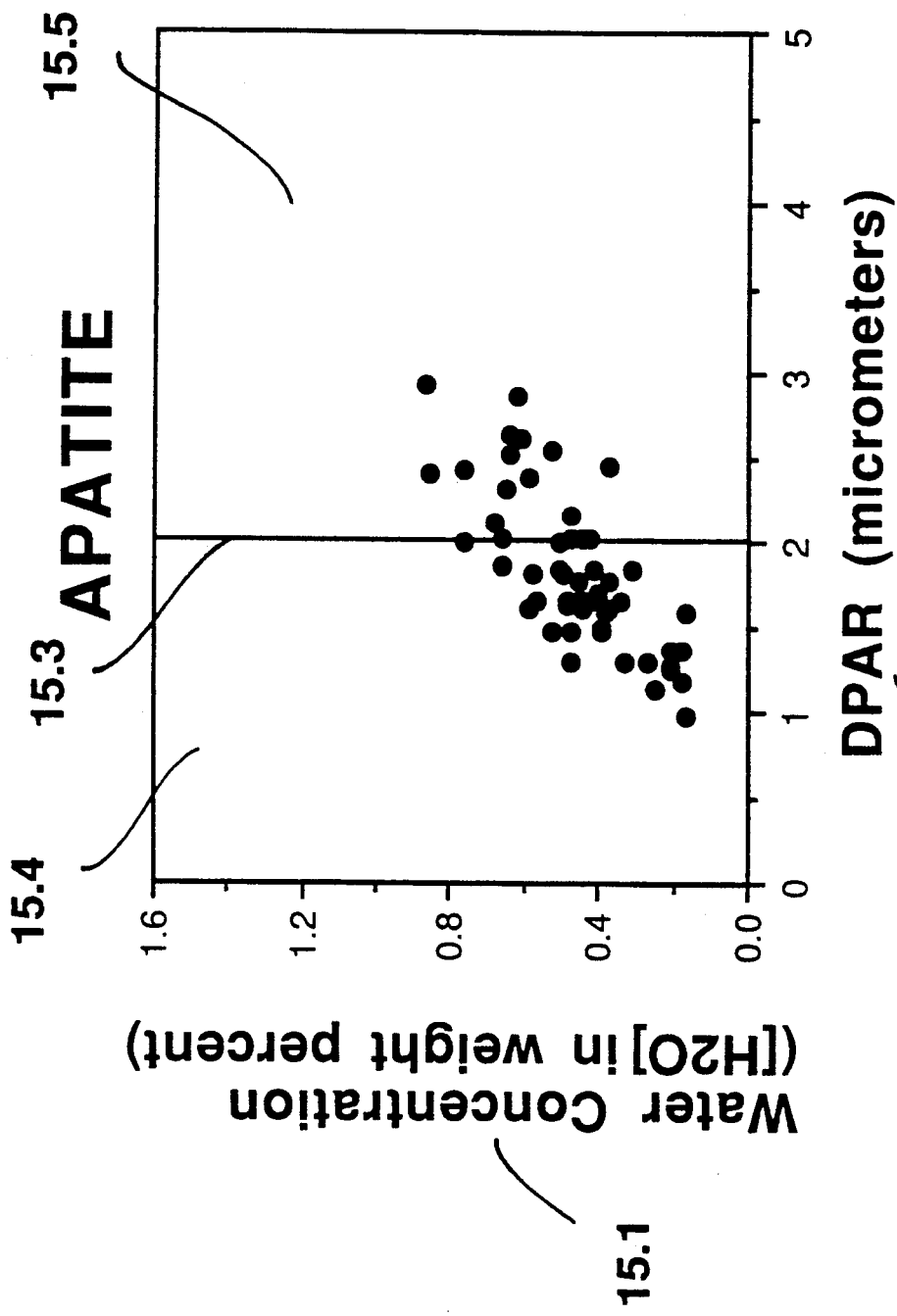
FIG. 15 is a plot of water concentration [H2O] (in units of weight percent) of selected age grains and a fraction of the selected length grains from FIGS. 11 and 12 as a function of the arithmetic mean maximum etch figure diameter parallel to the crystallographic c-axis, DPAR (in units of micrometers).

The mean maximum etch FIG. 5.4 diameters parallel 9.8 and perpendicular 9.9 to the crystallographic c-axis 9.7 of the selected age grains 5.9 and selected length grains 5.10 are strongly correlated with the chemical composition of the apatite grain. This is illustrated in FIGS. 13, 14, and 15, where values of fluorine concentration 13.1 (or [F]), chlorine concentration 14.1 (or [Cl]), and water concentration 15.1 (or [H2O]), respectively, are plotted relative to DPAR, 13.2, 14.2, or 15.2, for a combination of the selected age grains 5.9 and a fraction of the selected length grains 5.10 previously used to construct FIGS. 11 and 12. The chemical formula for the mineral apatite is usually written as $Ca_5[(PO_4)]_3[F,Cl,OH]_1$ where it can usually be assumed that the mole fractions of fluorine (or F), chlorine (or Cl), and hydroxy (or OH) add up to a value of 1. At present, there are no published experimental data that demonstrate a significant dependence of fission track annealing behavior on variations in apatite chemistry, except for variations in the amounts of fluorine, chlorine, and water (or hydroxy) present. The values of [F] 13.1, [Cl] 14.1, and [H2O] 15.1 plotted in FIGS. 13, 14, and 15, in conventionally used units of weight percent, were determined using an electron microprobe. Equations have been fitted to the data comprising these 3 plots, using a least-squares fitting criterion, and they give the following correlations of [F] 13.1, [Cl] 14.1, and [H2O] 15.1 in the apatite grains with DPAR, 13.2, 14.2, or 15.2:

| | |
|---|---|
| [F] = 4.6748 − 1.3106 DPAR + 0.041759 DPAR$^2$ | $R^2$ = 0.765 |
| [Cl] = −0.31045 − 0.053515 DPAR + 0.26067 DPAR$^2$ | $R^2$ = 0.806 |
| [H2O] = −0.048074 + 0.28092 DPAR | $R^2$ = 0.560 | where:

[F], in units of weight percent, is the fluorine concentration 13.1 in the selected age grains 5.9 and a fraction of the selected length grains 5.10 for which microprobe data were obtained,

[Cl], in units of weight percent, is the chlorine concentration 14.1 in the selected age grains 5.9 and a fraction of the selected length grains 5.10 for which microprobe data were obtained,

[H2O], in units of weight percent, is essentially the water concentration 15.1 in the selected age grains 5.9 and a fraction of the selected length grains 5.10 for which microprobe data were obtained, DPAR 13.2, 14.2, 15.2, in units of length, is the arithmetic mean maximum etch FIG. 5.4 diameter parallel 9.8 to the crystallographic c-axis 9.7 of the selected age grains 5.9 and a fraction of the selected length grains 5.10 for which microprobe data were obtained; and $R^2$, having no units, is the squared correlation coefficient between [F] 13.1, [Cl] 14.1, and [H2O] 15.1, respectively, and DPAR 13.2, 14.2, 15.2 for each plot.

Plots similar to FIGS. 13, 14, and 15 can be constructed to show the correlations of [F] 13.1, [Cl] 14.1, and [H2O] 15.1 with DPER, the arithmetic mean etch FIG. 5.4 diameter perpendicular 9.9 to the crystallographic c-axis in the apatite grains.

It is clear from the plots in FIGS. 13, 14, and 15 and from the squared correlation coefficients (the squared correlation coefficient for a perfect correlation equals 1.0) for the 3 equations that DPAR, 13.2, 14.2, and 15.2, the etch FIG. 5.4 diameter parallel 9.8 to the crystallographic c-axis 9.7, is strongly controlled by changes in the concentrations of [F] 13.1, [Cl] 14.1, and [H2O] 15.1. Furthermore, the strongest correlation exists between DPAR 14.2 and [Cl] 14.1, which correlation has a squared correlation coefficient closest to 1.0. Abundant published experimental data demonstrate that variations in [Cl] 14.1 in apatite give rise to the greatest variations in fission track annealing behavior in apatite.

The plots in FIGS. 13, 14, and 15 permit fluorine-rich apatite grains to be distinguished from relatively non-fluorine-rich apatite grains based on measured values of DPAR, 13.2, 14.2, and 15.2. Fluorine-rich apatite grains exhibit values of DPAR, 13.2, 14.2, 15.2 less than or equal to 2.0 micrometers whereas relatively non-fluorine-rich apatite grains exhibit values of DPAR greater than 2.0 micrometers. In each plot, a vertical line at DPAR equal to 2.0 micrometers 13.3, 14.3, and 15.3 has been drawn to separate the field of fluorine-rich grains 13.4, 14.4, and 15.4 from the field of relatively non-fluorine-rich grains 13.5, 14.5, and 15.5. It is possible to preserve the nature of the continuum of chemical compositional data among these selected age grains 5.9 and selected length grains 5.10, for example by using the above equations, but for the purpose of the discussion which follows, discrete groups are used.

Referring to FIG. 11 again, it is possible to classify each selected age grain 5.9 as either fluorine-rich 11.4, if it possesses a value of DPAR 11.2 less than or equal to 2.0 micrometers 11.3, or relatively non-fluorine-rich 11.5, if it possesses a value of DPAR 11.2 greater than 2.0 micrometers 11.3. Once the fluorine-rich 11.4 and relatively non-fluorine-rich 11.5 selected age grains 5.9 are grouped, a pooled fission track age is calculated for the fluorine-rich 11.4 pool of selected age grains 5.9 and the relatively non-fluorine-rich 11.5 pool of selected age grains 5.9. A pooled fission track age is calculated using the sum of the naturally occurring fission tracks, the sum of the induced fission tracks, and the sum of the apatite surface areas analyzed, for the selected age grains 5.9 being pooled, in the previously described equations.

A statistical test is then performed to determine if the fluorine-rich 11.4 selected age grains 5.9 are consistent with the notion that they have recorded a single thermal history. If the fluorine-rich 11.4 selected age grains 5.9 pass this statistical test and they are consistent with having recorded a single thermal history, then it is possible to use the pooled fission track age for the fluorine-rich 11.4 selected age grains 5.9 to interpret the thermal history of the rock sample from which the selected age grains 5.9 were separated using and available methods. Similarly, a statistical test is performed to determine if the relatively nonfluorine-rich 11.5 selected age grains 5.9 are consistent with the notion that they have recorded a single thermal history. If the relatively non-fluorine-rich 11.5 selected age grains 5.9 pass this statistical test and they are consistent with having recorded a single thermal history, then it is possible to use the pooled fission track age for the relatively non-fluorine-rich 11.5 selected age grains 5.9 to interpret the thermal history of the rock sample from which the selected age grains 5.9 were separated using currently available methods.

The currently used and generally available methods of interpreting fission track data measured for fluorine-rich 11.4 selected age grains 5.9 may use, as additional input into the computer algorithms, the pooled distribution (not shown) of perceived track lengths 5.11 measured for only fluorine-rich selected length grains 5.10. Referring back to FIG. 12, the perceived track lengths 12.1 measured in fluorine-rich 12.4 selected length grains 5.10, such selected length grains 12.4 exhibiting values of DPAR 12.2 less than or equal to 2.0 micrometers 12.3, may be pooled into a single distribution (not shown) for the purpose of interpreting the thermal history of the rock sample from which the selected length grains 5.10 were obtained. Similarly, the currently used and generally available methods of interpreting fission track data measured for relatively non-fluorine-rich 11.5 selected age grains 5.9 may use, as additional input into the computer algorithms, the pooled distribution (not shown) of perceived track lengths 12.1 measured for only relatively non-fluorine-rich 12.5 selected length grains 5.10; such relatively non-fluorine-rich 12.5 selected length grains 5.10 exhibit values of DPAR 12.2 greater than 2.0 micrometers 12.3.

For a series of selected age grains 5.9 and selected length grains 5.10 that, combined, exhibit a significant range in DPAR 11.2 and 12.2 values, the grains with the smallest DPAR 11.2 and 12.2 values are those that are closest to the pure fluorapatite composition. Selected age grains 5.9 and selected length grains 5.10 that possess significantly larger DPAR 11.2 and 12.2 values, in comparison to the group having the smallest DPAR 11.2 and 12.2 values, are likely to possess relatively greater amounts of chlorine and/or water. It is difficult to determine the amounts of chlorine and water in selected age grains 5.9 and selected length grains 5.10 with relatively large DPAR 11.2 and 12.2 values but it is apparent that more chlorine-rich apatites have larger DPER 9.9 values, the arithmetic mean etch FIG. 5.4 diameter perpendicular 9.9 to the crystallographic c-axis 9.7, in comparison to selected age grains 5.9 and selected length grains 5.10 which are predominantly water-rich.

The classification of the selected age grains 5.9 and selected length grains 5.10 as either fluorine-rich 11.4 and 12.4 or nonfluorine-rich 11.5 and 12.5 is important due to the tendency of the fission tracks in fluorine-rich apatite 11.4 and 12.4 to completely anneal after 1 million years or so, at a temperature in the range of approximately 110° to 120° Celsius. This temperature is well known to oil and gas explorationists as a critical temperature for oil formation. When rock formations are heated as hot as approximately 100° Celsius, they tend to generate or bear oil and/or associated hydrocarbon resources; when rock formations are heated above 110° to 120° Celsius, they tend to bear natural gas and/or associated hydrocarbon resources.

Fission tracks in relatively non-fluorine-rich 11.5 and 12.5 selected age grains 5.9 and selected length grains 5.10 completely anneal, after 1 million years or so, at a temperature in the range of approximately 120° to 150° Celsius. The temperature of 150° Celsius is also a well known temperature to oil and gas explorationists because rock formations heated significantly above this temperature are over mature, meaning that they are higher risk prospects for exploration.

Available computer models currently in use by the geochemical, geophysical, and petrochemical exploration community that utilize fission track age and perceived track length 5.11 data or otherwise perform calculations relevant to such data require that the data be obtained from a single selected age grain 5.9 and selected length grain 5.10, or a population (not shown) of selected age grains 5.9 and selected length grains 5.10 that are characterized by a single chemical composition or narrow range in chemical compositions, and a single recorded thermal history. As previously described for the example illustrated in FIGS. 6, 11, and 12, this sample fails both requirements of the computer models. Lacking expensive microprobe data for all of the selected length grains 5.10 in FIG. 12, and prior to the present invention, an interpretation of this sample using available computer models would be erroneous because the sample violates the rules for the use of these programs. As such, the data obtained are essentially useless without the benefit of chemical composition data for each selected length grain 5.10 studied.

The present invention allows an inexpensive and adequate interpretation of this sample to be made using presently available computer models. Referring to FIG. 11, there exists a strong clustering of apatite grain ages 11.1 having values very close to 0 Ma (million years) for the selected age grains 5.9 possessing DPAR 11.2 values of 2.0 micrometers or less. These selected age grains 5.9 fall into the fluorine-rich 11.4 field and pooling these selected age grains 5.9, as described above, satisfies the condition that the grains exhibit a narrow range in chemical composition. Furthermore, when population statistics are applied to the individual fission track ages 11.1 of the selected age grains 5.9 in the fluorine-rich 11.4 field, there exists strong statistical evidence that the fission tracks that they contain record a single thermal history. Having met both of the requirements for the utilization of the available computer models for interpreting fission track data in apatite, a model can be applied to the fluorine-rich 11.4 selected age grains 5.9 for this sample using the pooled fission track age and pooled distribution (not shown) of perceived track lengths 5.11 obtained by pooling the perceived track lengths 12.1 in FIG. 12 measured on selected length grains 5.10 that also lie in the fluorine-rich 12.4 field. This analysis proves to be very useful to the client explorationist because a good analysis helps elucidate critical information regarding prospect risk during hydrocarbon exploration.

I claim:

1. A method of determining the geological evolution of apatite grains contained within rock samples comprising obtaining a sufficiently pure quantity of representative apatite grains from a rock sample;

forming at least one epoxy wafer containing said representative apatite grains for examination and polishing said epoxy wafer containing said representative apatite grains in order to expose internal planar surfaces of the apatite grains;

chemically etching naturally occurring fission tracks and other crystallographic imperfections that intersect the polished internal planar surfaces of the said apatite grains with an acidic solution;

selecting a first-set of apatite grains from among suitable candidate apatite grains for fission track age measurement;

determining the density of naturally occurring fission tracks of said first-set apatite grains;

measuring the maximum diameters of etch figures formed by the intersection of said etched naturally occurring fission tracks and other crystallographic imperfections with the etched internal planar surfaces of the first-set apatite grains, said diameters being parallel to the crystallographic c-axes of the said first-set apatite grains, and calculating the arithmetic mean of the etch figure diameters parallel to the c-axis for each first-set apatite grain;

measuring the maximum diameters of etch figures formed by the intersection of said etched naturally occurring fission tracks and other crystallographic imperfections with the etched internal planar surfaces of the first-set apatite grains, said diameters being perpendicular to the crystallographic c-axes of the said first-set apatite grains, and calculating the arithmetic mean of the etch figure diameters perpendicular to the c-axis for each first-set apatite grain;

selecting a second-set of apatite grains from among suitable candidate apatite grains for measurement of perceived track lengths of confined fission tracks;

measuring the perceived track lengths of confined naturally occurring fission tracks within the second-set apatite grains;

measuring the maximum diameters of etch figures formed by the intersection of said etched naturally occurring fission tracks and other crystallographic imperfections with the etched internal planar surfaces of the second-set apatite grains, said diameters being parallel to the crystallographic c-axes of the said second-set apatite grains, and calculating the arithmetic mean of the etch figure diameters parallel to the c-axis for each second-set apatite grain;

measuring the maximum diameters of etch figures formed by the intersection of said etched naturally occurring fission tracks and other crystallographic imperfections with the etched internal planar surfaces of the second-set apatite grains, said diameters being perpendicular to the crystallographic c-axes of the said second-set apatite grains, and calculating the arithmetic mean of the etch figure diameters perpendicular to the c-axis for each second-set apatite grain;

determining the concentration of $^{238}U$ for the first-set apatite grains;

determining the fission track ages of the first-set apatite grains;

determining the chemical composition of first-set and second-set apatite grains;

calculating the pooled fission track age and pooled distribution of perceived track lengths of fluorine-rich first-set and fluorine-rich second-set apatite grains; and calculating the pooled fission track age and pooled distribution of perceived track lengths of relatively non-fluorine-rich first-set and relatively non-fluorine-rich second-set apatite grains.

2. A method according to claim 1 including forming at least one epoxy wafer containing said representative apatite grains for examination and polishing said epoxy wafer containing said representative apatite grains in order to expose internal planar surfaces of the apatite grains comprises spreading the representative apatite grains on a non-stick surface within an area of approximately one square centimeter defined by a form which is 1.5 millimeters deep and in contact with the non-stick surface;

pouring a mix of epoxy resin and epoxy hardener over the sampling of representative apatite grains contained within the form;

placing a petrographic microscope slide on top of the epoxy resin and applying a slight downward force to ensure that said slide will be attached to the epoxy resin;

allowing the epoxy resin mix to harden for twenty four hours at room temperature thereby forming an epoxy wafer;

detaching the resulting epoxy wafer from the non-stick surface while allowing the epoxy wafer to remain attached to the petrographic microscope slide; and polishing the planar surface of the resulting epoxy wafer opposite that attached to the petrographic slide to an extremely smooth finish thereby removing a portion of the epoxy wafer and a similar thickness of the apatite grains aligned with the planar surface being polished thereby exposing internal surfaces of the apatite grains.

3. A method according to claim 1 including chemically etching naturally occurring fission tracks and other crystallographic imperfections that intersect the polished internal planar surfaces of the said apatite grains with an acidic solution comprises immersing the epoxy wafer and attached petrographic slide in an acidic solution whereby all naturally occurring fission tracks and other crystallographic imperfections exposed to the acidic solution will be chemically etched;

removing the epoxy wafer and attached petrographic slide from the solution;

washing the epoxy wafer and attached petrographic slide with distilled water; and drying the epoxy wafer and attached petrographic slide sufficiently to remove all fluid from the resulting etch pits.

4. A method according to claim 3 including said epoxy wafer and attached petrographic slide are immersed in a nitric acid solution of 5.5 Molar strength at 21 degrees Celsius for 20 seconds while being swirled vigorously within the solution.

5. A method according to claim 1 including selecting a first-set of apatite grains from among suitable candidate apatite grains for fission track age measurement comprises observing the etched apatite grains contained within the polished and etched surface of the epoxy wafer and identifying suitable candidate apatite grains for fission track age measurement which have their crystallographic c-axes oriented parallel to the polished and etched planar surface of the epoxy wafer; and selecting apatite grains from among the suitable candidate apatite grains possessing a relatively high fraction of etch pits that represent etched naturally occurring fission tracks in combination with a relatively large available etched surface area.

6. A method according to claim 1 including determining the density of naturally occurring fission tracks of said first-set apatite grains comprises viewing the first-set apatite grains through a magnifying device possessing a graticule grid of known dimensions and which is imposed upon viewed images;

counting the number of etch figures resulting from the intersection of etch pits that represent etched naturally occurring fission tracks with the etched planar surface within an area of known dimensions defined by the graticule grid; and calculating the spontaneous fission track density according to the formula:

$$\rho_S = N_S/AREA$$

where $N_S$, in units of tracks, is the number of etch figures created by the intersection of etch pits that represent etched naturally occurring fission tracks with the etched planar surface of the first-set apatite grain within the area outlined by a portion of the graticule grid; and where AREA, in units of length squared, is the area of the surface of the first-set grain outlined by the graticule grid.

7. A method according to claim 1 including measuring the maximum diameters of etch figures formed by the intersection of said etched naturally occurring fission tracks and other crystallographic imperfections with the etched internal planar surfaces of the first-set apatite grains, said diameters being parallel to the crystallographic c-axes of the said first-set apatite grains, and calculating the arithmetic mean of the etch figure diameters parallel to the c-axis for each first-set apatite grain comprises viewing the first-set apatite grains through a magnifying device;

placing the point source of light from a cursor apparatus attached to a digitizing tablet at precisely one extreme of the diameter parallel to the crystallographic c-axis of each etch figure and electronically recording the coordinates, $X_1, Y_1$, of the point;

placing the point source of light from the cursor apparatus at precisely the opposite extreme of the diameter parallel to the crystallographic c-axis of each etch figure and electronically recording the coordinates, $X_2, Y_2$, of the point;

calculating the length of the maximum diameter parallel to the crystallographic c-axis of each etch figure using the formula:

$$DPAR_i = C \; sqrt \; ((X_2 - X_1)^2 + (Y_2 - Y_1)^2)$$

where $DPAR_i$, in units of length, is the numerical value of the length of the maximum etch figure diameter parallel to the crystallographic c-axis of the i-th etch figure on the etched planar surface of the first-set apatite grain being studied; and where C is a scaling factor that converts the units of the digitizing tablet into units of length; and calculating the arithmetic mean of the etch figure diameters parallel to the crystallographic c-axis for each first-set apatite grain studied by summing all values of $DPAR_i$ measured for each first-set apatite grain and dividing the resultant sum by the number of etch figure diameters measured.

8. A method according to claim 1 including measuring the maximum diameters of etch figures formed by the intersection of said etched naturally occurring fission tracks and other crystallographic imperfections with the etched internal planar surfaces of the first-set apatite grains, said diameters being perpendicular to the crystallographic c-axes of the said first-set apatite grains, and calculating the arithmetic mean of the etch figure diameters perpendicular to the c-axis for each first-set apatite grain comprises viewing the first-set apatite grains through a magnifying device;

placing the point source of light from a cursor apparatus attached to a digitizing tablet at precisely one extreme of the diameter perpendicular to the crystallographic c-axis of each etch figure and electronically recording the coordinates, $X_3, Y_3$, of the point;

placing the point source of light from the cursor apparatus at precisely the opposite extreme of the diameter perpendicular to the crystallographic c-axis of each etch figure and electronically recording the coordinates, $X_4, Y_4$, of the point;

calculating the length of the maximum diameter perpendicular to the crystallographic c-axis of each etch figure using the formula:

$$DPER_i = C \; sqrt \; ((X_4 - X_3)^2 + (Y_4 - Y_3)^2)$$

where $DPER_i$, in units of length, is the numerical value of the length of the maximum etch figure diameter perpendicular to the crystallographic c-axis of the i-th etch figure on the etched planar surface of the first-set apatite grain being studied; and where C is a scaling factor that converts the units of the digitizing tablet into units of length; and calculating the arithmetic mean of the etch figure diameters perpendicular to the crystallographic c-axis for each first-set apatite grain studied by summing all values of $DPER_i$ measured for each first-set apatite grain and dividing the resultant sum by the number of etch figure diameters measured.

9. A method according to claim 1 including selecting a second-set of apatite grains from among suitable candidate apatite grains for measurement of perceived track lengths of confined fission tracks comprises observing the etched apatite grains contained within the polished and etched surface of the epoxy wafer and identifying suitable candidate apatite grains that contain etched confined fission tracks and which have their crystallographic c-axes oriented parallel to the polished and etched planar surface of the epoxy wafer; and identifying as many as 200 confined fission tracks which are etched to their ends and which lie within approximately 10 degrees of parallel to the polished and etched planar surface of the apatite grains.

10. A method according to claim 1 including measuring the perceived track lengths of confined naturally occurring fission tracks within the second-set apatite grains comprises viewing the second-set apatite grains under a binocular optical microscope having multiple illuminating light sources, and a projection tube by which a point source of light from a cursor apparatus attached to a digitizing tablet can be visually observed while looking through the microscope;

placing the point source of light from a cursor apparatus attached to a digitizing tablet at precisely one extreme of each linear etched confined fission track, wholly contained within a second-set apatite grain, and electronically recording the coordinates, $X_5,Y_5$, of the point;

placing the point source of the light from the cursor apparatus at precisely the opposite extreme of each linear etched confined fission track, wholly contained within a second-set apatite grain, and electronically recording the coordinates, $X_6,Y_6$, of the point; and calculating the perceived track length of each linear etched confined fission track, wholly contained within the second-set apatite grains, according to the formula:

$$TL = C\ sqrt((X_6 - X_5)^2 + (Y_6 - Y_5)^2)$$

where TL, in units of length, is the perceived track length of a confined fission track in a second-set apatite grain; and where C, in units of length, is a scaling factor that converts the units of the digitizing tablet into units of length.

11. A method according to claim 1 including measuring the maximum diameters of etch figures formed by the intersection of said etched naturally occurring fission tracks and other crystallographic imperfections with the etched internal planar surfaces of the second-set apatite grains, said diameters being parallel to the crystallographic c-axes of the said second-set apatite grains, and calculating the arithmetic mean of the etch figure diameters parallel to the c-axis for each second-set apatite grain comprises viewing the second-set apatite grains through a magnifying device;

placing the point source of light from a cursor apparatus attached to a digitizing tablet at precisely one extreme of the diameter parallel to the crystallographic c-axis of each etch figure and electronically recording the coordinates, $X_1,Y_1$, of the point;

placing the point source of light from the cursor apparatus at precisely the opposite extreme of the diameter parallel to the crystallographic c-axis of each etch figure and electronically recording the coordinates, $X_2,Y_2$, of the point;

calculating the length of the maximum diameter parallel to the crystallographic c-axis of each etch figure using the formula:

$$DPAR_i = C\ sqrt\ ((X_2 - X_1)^2 + (Y_2 - Y_1)^2)$$

where $DPAR_i$, in units of length, is the numerical value of the length of the maximum etch figure diameter parallel to the crystallographic c-axis of the i-th etch figure on the etched planar surface of the second-set apatite grain being studied; and where C is a scaling factor that converts the units of the digitizing tablet into units of length; and calculating the arithmetic mean of the etch figure diameters parallel to the crystallographic c-axis for each second-set apatite grain studied by summing all values of $DPAR_i$ measured for each second-set apatite grain and dividing the resultant sum by the number of etch figure diameters measured.

12. A method according to claim 1 including measuring the maximum diameters of etch figures formed by the intersection of said etched naturally occurring fission tracks and other crystallographic imperfections with the etched internal planar surfaces of the second-set apatite grains, said diameters being perpendicular to the crystallographic c-axes of the said second-set apatite grains, and calculating the arithmetic mean of the etch figure diameters perpendicular to the c-axis for each second-set apatite grain comprises viewing the second-set apatite grains through a magnifying device;

placing the point source of light from a cursor apparatus attached to a digitizing tablet at precisely one extreme of the diameter perpendicular to the crystallographic c-axis of each etch figure and electronically recording the coordinates, $X_3,Y_3$, of the point;

placing the point source of light from the cursor apparatus at precisely the opposite extreme of the diameter perpendicular to the crystallographic c-axis of each etch figure and electronically recording the coordinates, $X_4,Y_4$, of the point;

calculating the length of the maximum diameter perpendicular to the crystallographic c-axis of each etch figure using the formula:

$$DPER_i = C\ sqrt\ ((X_4 - X_3)^2 + (Y_4 - Y_3)^2)$$

where $DPER_i$, in units of length, is the numerical value of the length of the maximum etch figure diameter perpendicular to the crystallographic c-axis of the i-th etch figure on the etched planar surface of the second-set apatite grain being studied; and where C is a scaling factor that converts the units of the digitizing tablet into units of length; and calculating the arithmetic mean of the etch figure diameters perpendicular to the crystallographic c-axis for each second-set apatite grain studied by summing all values of DPERi measured for each second-set apatite grain and dividing the resultant sum by the number of etch figure diameters measured.

13. A method according to claim 1 including the determination of the concentration of $^{238}$U for first-set apatite grains comprises placing a muscovite mica detector in intimate contact with the etched planar surface of the epoxy wafer containing the first-set apatite grains;

placing the epoxy wafer and muscovite mica detector in close proximity to the core of a nuclear reactor;

placing a portion of uranium-doped glass in intimate contact with a muscovite mica detector in close proximity to the core of a nuclear reactor;

irradiating the epoxy wafer and the uranium-doped glass and their respective muscovite mica masks with thermal neutrons thereby inducing fission of $^{235}$U in the first-set apatite grains within the epoxy wafer and the uranium-doped glass;

removing the epoxy wafer, uranium-doped glass, and muscovite mica detectors from close proximity to the core of a nuclear reactor;

chemically etching the induced fission tracks within the muscovite mica detectors;

calculating the concentration of $^{238}$U for each first-set apatite grain according to the formula:

$$[^{238}U] = 137.88 \, [^{235}U_g] \, (R_g/R_a) \, (P_{ia}/P_{ig})$$

where $[^{238}U]$, in units of nuclei per length cubed, is the concentration of the uranium isotope $^{238}$U in a first-set apatite grain within the apatite volume of interest;

where 137.88, in units of nuclei per nuclei, is a constant for all first-set apatite grains which represents the naturally occurring concentration ratio of the uranium isotopes $^{238}$U to $^{235}$U;

where $[^{235}U_g]$, in units of nuclei per length cubed, is the concentration of the uranium isotope $^{235}$U in the uranium-doped glass;

where $R_g$, in units of length, is the average distance travelled by a single fission fragment nucleus in the uranium-doped glass;

where $R_a$, in units of length, is the average distance travelled by a single fission fragment nucleus in the first-set apatite grain;

where $P_{ia}$, in units of tracks per length squared, is the surface density of induced fission track etch pits that cross the etched planar surface of the detector within the area of the detector outlined by the graticule grid that was in intimate contact with the previously studied area of the first-set apatite grain; and where $P_{ig}$, in units of tracks per length squared, is the surface density of induced fission track etch pits that cross the etched planar surface of the detector that was in intimate contact with the uranium-doped glass.

14. A method according to claim 1 including determining the fission track age of said first-set apatite grains comprises calculating the fission track age for each first-set apatite grain using the formula:

$$T = (1/l_D) \, \ln((l_D/l_F)([FT]/[^{238}U]) + 1)$$

where T, in units of millions of years, is the fission track age for the first-set apatite grain;

where $l_D$, in units of nuclei per million years, is the total decay constant for $^{238}$U;

where $l_F$, in units of nuclei per million years, is the fission decay constant for $^{238}$U;

where [FT], in units of tracks per length cubed, is the number of naturally occurring fission tracks, resulting from the spontaneous fission decay of $^{238}$U, per unit volume of interest in the first-set apatite; and where $[^{238}U]$, in units of nuclei per length cubed, is the concentration of the uranium isotope $^{238}$U in the first-set apatite grain within the apatite volume of interest.

15. A method according to claim 1 including determining the chemical composition of the first-set and second-set apatite grains comprises plotting the individual apatite grain ages of the first-set apatite grains as a function of the arithmetic mean maximum etch figure diameter parallel to the crystallographic c-axis;

plotting the individual track lengths of the second-set apatite grains as a function of the arithmetic mean maximum etch figure diameter parallel to the crystallographic c-axis;

grouping each of the first-set apatite grains and second-set apatite grains into either a group which is predominantly composed of fluorine-rich apatite or a group which is predominantly composed of relatively non-fluorine-rich apatite by determining whether the arithmetic mean maximum etch figure diameter parallel to the crystallographic c-axis on the planar surface of the apatite grain is less than or equal to a length of 2 micrometers, in the case of fluorine-rich apatite, or greater than 2 micrometers, in the case of relatively non-fluorine-rich apatite.

16. A method according to claim 1 including determining the chemical composition of the first-set and second-set apatite grains comprises calculating the fluorine concentration or [F] for first-set and second-set apatite grains according to the following formula:

$$[F] = 4.6748 - 1.3106 \, DPAR + 0.041759 \, DPAR^2$$

where [F], in units of weight percent, is the fluorine concentration in the first-set or second-set apatite grain being studied; and where DPAR, in units of length, is the arithmetic mean maximum etch figure diameter parallel to the crystallographic c-axis in the first-set or second-set apatite grain being studied.

17. A method according to claim 1 including determining the chemical composition of the first-set and second-set apatite grains comprises calculating the chlorine concentration or [Cl] for first-set and second-set apatite grains according to the following formula:

$$[Cl] = -0.31045 - 0.053515 \, DPAR + 0.26067 \, DPAR^2$$

where [Cl], in units of weight percent, is the chlorine concentration in the first-set or second-set apatite grain being studied; and where DPAR, in units of length, is the arithmetic mean maximum etch figure diameter parallel to the crystallographic c-axis in the first-set or second-set apatite grain being studied.

18. A method according to claim 1 including determining the chemical composition of the first-set and second-set apatite grains comprises calculating the water concentration or [H2O] for first-set and second-set apatite grains according to the following formula:

$$[H_2O] = -0.048074 + 0.28092 \, DPAR$$

where [H2O], in units of weight percent, is the water concentration in the first-set or second-set apatite grain being studied; and where DPAR, in units of length, is the arithmetic mean maximum etch figure diameter parallel to the crystallographic c-axis in the first-set or second-set apatite grain being studied.

19. A method of determining the chemical composition of apatite grains contained within rock samples comprising obtaining a sufficiently pure quantity of representative apatite grains from a rock sample;

forming at least one epoxy wafer containing said representative apatite grains for examination and polishing said epoxy wafer containing said representative apatite grains in order to expose internal planar surfaces of the apatite grains;

chemically etching naturally occurring fission tracks and other crystallographic imperfections that intersect the polished internal planar surfaces of the said apatite grains with an acidic solution;

selecting a first-set of apatite grains from among suitable candidate apatite grains;

measuring the maximum diameters of etch figures formed by the intersection of said etched naturally occurring fission tracks and other crystallographic imperfections with the etched internal planar surfaces of the first-set apatite grains, said diameters being parallel to the crystallographic c-axes of the said first-set apatite grains, and calculating the arithmetic mean of the etch figure diameters parallel to the c-axis for each first-set apatite grain;

measuring the maximum diameters of etch figures formed by the intersection of said etched naturally occurring fission tracks and other crystallographic imperfections with the etched internal planar surfaces of the first-set apatite grains, said diameters being perpendicular to the crystallographic c-axes of the said first-set apatite grains, and calculating the arithmetic mean of the etch figure diameters perpendicular to the c-axis for each first-set apatite grain;

selecting a second-set of apatite grains from among suitable candidate apatite grains;

measuring the maximum diameters of etch figures formed by the intersection of said etched naturally occurring fission tracks and other crystallographic imperfections with the etched internal planar surfaces of the second-set apatite grains, said diameters being parallel to the crystallographic c-axes of the said second-set apatite grains, and calculating the arithmetic mean of the etch figure diameters parallel to the c-axis for each second-set apatite grain;

measuring the maximum diameters of etch figures formed by the intersection of said etched naturally occurring fission tracks and other crystallographic imperfections with the etched internal planar surfaces of the second-set apatite grains, said diameters being perpendicular to the crystallographic c-axes of the said second-set apatite grains, and calculating the arithmetic mean of the etch figure diameters perpendicular to the c-axis for each second-set apatite grain; and determining the chemical composition of first-set and second-set apatite grains.

20. A method according to claim 19 including forming at least one epoxy wafer containing said representative apatite grains for examination and polishing said epoxy wafer containing said representative apatite grains in order to expose internal planar surfaces of the apatite grains comprises spreading the representative apatite grains on a non-stick surface within an area of approximately one square centimeter defined by a form which is 1.5 millimeters deep and in contact with the non-stick surface;

pouring a mix of epoxy resin and epoxy hardener over the sampling of representative apatite grains contained within the form;

placing a petrographic microscope slide on top of the epoxy resin and applying a slight downward force to ensure that said slide will be attached to the epoxy resin;

allowing the epoxy resin mix to harden for twenty four hours at room temperature thereby forming an epoxy wafer;

detaching the resulting epoxy wafer from the non-stick surface while allowing the epoxy wafer to remain attached to the petrographic microscope slide; and polishing the planar surface of the resulting epoxy wafer opposite that attached to the petrographic slide to an extremely smooth finish thereby removing a portion of the epoxy wafer and a similar thickness of the apatite grains aligned with the planar surface being polished thereby exposing internal surfaces of the apatite grains.

21. A method according to claim 19 including chemically etching naturally occurring fission tracks and other crystallographic imperfections that intersect the polished internal planar surfaces of the said apatite grains with an acidic solution comprises immersing the epoxy wafer and attached petrographic slide in an acidic solution whereby all naturally occurring fission tracks and other crystallographic imperfections exposed to the acidic solution will be chemically etched;

removing the epoxy wafer and attached petrographic slide from the solution;

washing the epoxy wafer and attached petrographic slide with distilled water; and drying the epoxy wafer and attached petrographic slide sufficiently to remove all fluid from the resulting etch pits.

22. A method according to claim 21 including said epoxy wafer and attached petrographic slide are immersed in a nitric acid solution of 5.5 Molar strength at 21 degrees Celsius for 20 seconds while being swirled vigorously within the solution.

23. A method according to claim 19 including selecting a first-set of apatite grains from among suitable candidate apatite grains comprises observing the etched apatite grains contained within the polished and etched surface of the epoxy wafer and identifying suitable candidate apatite grains which have their crystallographic c-axes oriented parallel to the polished and etched planar surface of the epoxy wafer; and selecting apatite grains from among the suitable candidate apatite grains possessing etch figures on their polished and etched planar surfaces.

24. A method according to claim 19 including measuring the maximum diameters of etch figures formed by the intersection of said etched naturally occurring fission tracks and other crystallographic imperfections with the etched internal planar surfaces of the first-set apatite grains, said diameters being parallel to the crystallographic c-axes of the said first-set apatite grains, and calculating the arithmetic mean of the etch figure diameters parallel to the c-axis for each first-set apatite grain comprises viewing the first-set apatite grains through a magnifying device;

placing the point source of light from a cursor apparatus attached to a digitizing tablet at precisely one extreme of the diameter parallel to the crystallographic c-axis of each etch figure and electronically recording the coordinates, $X_1, Y_1$, of the point;

placing the point source of light from the cursor apparatus at precisely the opposite extreme of the diameter parallel to the crystallographic c-axis of each etch figure and electronically recording the coordinates, $X_2, Y_2$, of the point;

calculating the length of the maximum diameter parallel to the crystallographic c-axis of each etch figure using the formula:

$$DPAR_i = C\ sqrt\ ((X_2-X_1)^2 + (Y_2-Y_1)^2)$$

where $DPAR_i$, in units of length, is the numerical value of the length of the maximum etch figure diameter parallel to the crystallographic c-axis of the i-th etch figure on the etched planar surface of the first-set apatite grain being studied; and where C is a scaling factor that converts the units of the digitizing tablet into units of length; and calculating the arithmetic mean of the etch figure diameters parallel to the crystallographic c-axis for each first-set apatite grain studied by summing all values of $DPAR_i$ measured for each first-set apatite grain and dividing the resultant sum by the number of etch figure diameters measured.

25. A method according to claim 19 including measuring the maximum diameters of etch figures formed by the intersection of said etched naturally occurring fission tracks and other crystallographic imperfections with the etched internal planar surfaces of the first-set apatite grains, said diameters being perpendicular to the crystallographic c-axes of the said first-set apatite grains, and calculating the arithmetic mean of the etch figure diameters perpendicular to the c-axis for each first-set apatite grain comprises viewing the first-set apatite grains through a magnifying device;

placing the point source of light from a cursor apparatus attached to a digitizing tablet at precisely one extreme of the diameter perpendicular to the crystallographic c-axis of each etch figure and electronically recording the coordinates, $X_3, Y_3$, of the point;

placing the point source of light from the cursor apparatus at precisely the opposite extreme of the diameter perpendicular to the crystallographic c-axis of each etch figure and electronically recording the coordinates, $X_4, Y_4$, of the point;

calculating the length of the maximum diameter perpendicular to the crystallographic c-axis of each etch figure using the formula:

$$DPER_i = C\ sqrt\ ((X_4-X_3)^2 + (Y_4-Y_3)^2)$$

where $DPER_i$, in units of length, is the numerical value of the length of the maximum etch figure diameter perpendicular to the crystallographic c-axis of the i-th etch figure on the etched planar surface of the first-set apatite grain being studied; and where C is a scaling factor that converts the units of the digitizing tablet into units of length; and calculating the arithmetic mean of the etch figure diameters perpendicular to the crystallographic c-axis for each first-set apatite grain studied by summing all values of $DPER_i$ measured for each first-set apatite grain and dividing the resultant sum by the number of etch figure diameters measured.

26. A method according to claim 19 including selecting a second-set of apatite grains from among suitable candidate apatite grains comprises observing the etched apatite grains contained within the polished and etched surface of the epoxy wafer and identifying suitable candidate apatite grains which have their crystallographic c-axes oriented parallel to the polished and etched planar surface of the epoxy wafer; and identifying suitable candidate apatite grains that contain confined fission tracks which are etched to their ends and which lie within approximately 10 degrees of parallel to the polished and etched planar surface of the apatite grains.

27. A method according to claim 19 including measuring the maximum diameters of etch figures formed by the intersection of said etched naturally occurring fission tracks and other crystallographic imperfections with the etched internal planar surfaces of the second-set apatite grains, said diameters being parallel to the crystallographic c-axes of the said second-set apatite grains, and calculating the arithmetic mean of the etch figure diameters parallel to the c-axis for each second-set apatite grain comprises viewing the second-set apatite grains through a magnifying device;

placing the point source of light from a cursor apparatus attached to a digitizing tablet at precisely one extreme of the diameter parallel to the crystallographic c-axis of each etch figure and electronically recording the coordinates, $X_1, Y_1$, of the point;

placing the point source of light from the cursor apparatus at precisely the opposite extreme of the diameter parallel to the crystallographic c-axis of each etch figure and electronically recording the coordinates, $X_2, Y_2$, of the point;

calculating the length of the maximum diameter parallel to the crystallographic c-axis of each etch figure using the formula:

$$DPAR_i = C \; sqrt \; ((X_2-X_1)^2 + (Y_2-Y_1)^2)$$

where $DPAR_i$, in units of length, is the numerical value of the length of the maximum etch figure diameter parallel to the crystallographic c-axis of the i-th etch figure on the etched planar surface of the second-set apatite grain being studied; and where C is a scaling factor that converts the units of the digitizing tablet into units of length; and calculating the arithmetic mean of the etch figure diameters parallel to the crystallographic c-axis for each second-set apatite grain studied by summing all values of $DPAR_i$ measured for each second-set apatite grain and dividing the resultant sum by the number of etch figure diameters measured.

28. A method according to claim 19 including measuring the maximum diameters of etch figures formed by the intersection of said etched naturally occurring fission tracks and other crystallographic imperfections with the etched internal planar surfaces of the second-set apatite grains, said diameters being perpendicular to the crystallographic c-axes of the said second-set apatite grains, and calculating the arithmetic mean of the etch figure diameters perpendicular to the c-axis for each second-set apatite grain comprises viewing the second-set apatite grains through a magnifying device;

placing the point source of light from a cursor apparatus attached to a digitizing tablet at precisely one extreme of the diameter perpendicular to the crystallographic c-axis of each etch figure and electronically recording the coordinates, $X_3, Y_3$, of the point;

placing the point source of light from the cursor apparatus at precisely the opposite extreme of the diameter perpendicular to the crystallographic c-axis of each etch figure and electronically recording the coordinates, $X_4, Y_4$, of the point;

calculating the length of the maximum diameter perpendicular to the crystallographic c-axis of each etch figure using the formula:

$$DPER_i = C \; sqrt \; ((X_4-X_3)^2 + (Y_4-Y_3)^2)$$

where $DPER_i$, in units of length, is the numerical value of the length of the maximum etch figure diameter perpendicular to the crystallographic c-axis of the i-th etch figure on the etched planar surface of the second-set apatite grain being studied; and where C is a scaling factor that converts the units of the digitizing tablet into units of length; and calculating the arithmetic mean of the etch figure diameters perpendicular to the crystallographic c-axis for each second-set apatite grain studied by summing all values of $DPER_i$ measured for each second-set apatite grain and dividing the resultant sum by the number of etch figure diameters measured.

29. A method according to claim 19 including determining the chemical composition of the first-set and second-set apatite grains comprises grouping each of the first-set apatite grains and second-set apatite grains into either a group which is predominantly composed of fluorine-rich apatite or a group which is predominantly composed of relatively non-fluorine-rich apatite by determining whether the arithmetic mean maximum etch figure diameter parallel to the crystallographic c-axis on the planar surface of the apatite grain is less than or equal to a length of 2 micrometers, in the case of fluorine-rich apatite, or greater than 2 micrometers, in the case of relatively non-fluorine-rich apatite.

30. A method according to claim 19 including determining the chemical composition of the first-set and second-set apatite grains comprises calculating the fluorine concentration or [F] for first-set and second-set apatite grains according to the following formula $$[F] = 4.6748 - 1.3106 \; DPAR + 0.041759 \; DPAR^2$$

where [F], in units of Weight percent, is the fluorine concentration in the first-set or second-set apatite grain being studied; and where DPAR, in units of length, is the arithmetic mean maximum etch figure diameter parallel to the crystallographic c-axis in the first-set or second-set apatite grain being studied.

31. A method according to claim 19 including determining the chemical composition of the first-set and second-set apatite grains comprises calculating the chlorine concentration or [Cl] for first-set and second-set apatite grains according to the following formula $$[Cl] = -0.31045 - 0.053515 \; DPAR + 0.26067 \; DPAR^2$$

where [Cl], in units of weight percent, is the chlorine concentration in the first-set or second-set apatite grain being studied; and where DPAR, in units of length, is the arithmetic mean maximum etch figure diameter parallel to the crystallographic c-axis in the first-set or second-set apatite grain being studied.

32. A method according to claim 19 including determining the chemical composition of the first-set and second-set apatite grains comprises calculating the water concentration or [H2O] for first-set and second-set apatite grains according to the following formula $$[H_2O] = -0.048074 + 0.28092 \; DPAR$$

where [H2O], in units of weight percent, is the water concentration in the first-set or second-set apatite grain being studied; and where DPAR, in units of length, is the arithmetic mean maximum etch figure diameter parallel to the crystallographic c-axis in the first-set or second-set apatite grain being studied.

* * * * *